(12) United States Patent
Mehrmohammadi et al.

(10) Patent No.: US 11,801,008 B2
(45) Date of Patent: Oct. 31, 2023

(54) ULTRASOUND, PHOTOACOUSTIC, AND VISCOELASTIC IMAGING SYSTEMS AND METHODS FOR CERVICAL ANALYSIS TO ASSESS RISK OF PRETERM DELIVERY

(71) Applicant: Wayne State University, Detroit, MI (US)

(72) Inventors: Mohammad Mehrmohammadi, Farmington Hills, MI (US); Sonia S. Hassan, Novi, MI (US); Edgar Hernandez-Andrade, Grosse Pointe Farm, MI (US); Yan Yan, Detroit, MI (US); Maryam Basij, Detroit, MI (US); Nardhy Gomez-Lopez, Detroit, MI (US)

(73) Assignee: Wayne State University, Detroit, MI (US)

( * ) Notice: Subject to any disclaimer, the term of this patent is extended or adjusted under 35 U.S.C. 154(b) by 842 days.

(21) Appl. No.: 16/659,720

(22) Filed: Oct. 22, 2019

(65) Prior Publication Data
US 2020/0121242 A1    Apr. 23, 2020

Related U.S. Application Data

(60) Provisional application No. 62/748,613, filed on Oct. 22, 2018.

(51) Int. Cl.
*A61B 5/00* (2006.01)
*A61B 8/08* (2006.01)
*A61B 8/00* (2006.01)

(52) U.S. Cl.
CPC .......... *A61B 5/4331* (2013.01); *A61B 5/0095* (2013.01); *A61B 5/7275* (2013.01);
(Continued)

(58) Field of Classification Search
CPC ... A61B 5/4331; A61B 5/0095; A61B 5/7275; A61B 8/0866; A61B 8/5223;
(Continued)

(56) References Cited

U.S. PATENT DOCUMENTS

2010/0222679 A1* 9/2010 Hall ................. A61B 8/483
600/443
2013/0210058 A1* 8/2013 White ................ A61B 5/443
435/29

(Continued)

OTHER PUBLICATIONS

Yah Yan et al, "Photoacoustic Imaging of The Uterine Cervix to Assess Collagen and Water Content Changes in Murine Pregnancy", vol. 10, No. 9 Biomedical Optics Express, Sep. 1, 2019.

*Primary Examiner* — Christopher Koharski
*Assistant Examiner* — James F McDonald
(74) *Attorney, Agent, or Firm* — Dinsmore & Shohl LLP

(57) ABSTRACT

Methods and system are described for multi-modal, multi-parametric, non-invasive, and real-time assessment of cervical tissue through a multi-modal probe device for use within a vaginal canal and an associated imaging system to assess a risk of preterm delivery of an expectant mother. The multi-modal system may include ultrasound (US) imaging, viscoelastic (VE) imaging, and/or photoacoustic (PA) imaging of the cervical issue to determine cervical biomarker information indicative of parameters including, but not limited to, a collagen to water ratio such that a more water dominant ratio is indicative of a risk of preterm delivery.

11 Claims, 20 Drawing Sheets

(52) U.S. Cl.
CPC .......... *A61B 8/0866* (2013.01); *A61B 8/5223* (2013.01); *A61B 5/435* (2013.01); *A61B 5/4343* (2013.01); *A61B 8/461* (2013.01)

(58) Field of Classification Search
CPC ......... A61B 8/461; A61B 5/0035; A61B 8/12; A61B 8/4416; A61B 5/435; A61B 5/4343
See application file for complete search history.

(56) References Cited

U.S. PATENT DOCUMENTS

| | | | |
|---|---|---|---|
| 2014/0276047 A1* | 9/2014 | Hall | A61B 8/12 600/449 |
| 2015/0150452 A1* | 6/2015 | Oraevsky | A61B 5/14546 600/440 |
| 2018/0271430 A1* | 9/2018 | Ramella-Roman | A61B 5/435 |

* cited by examiner

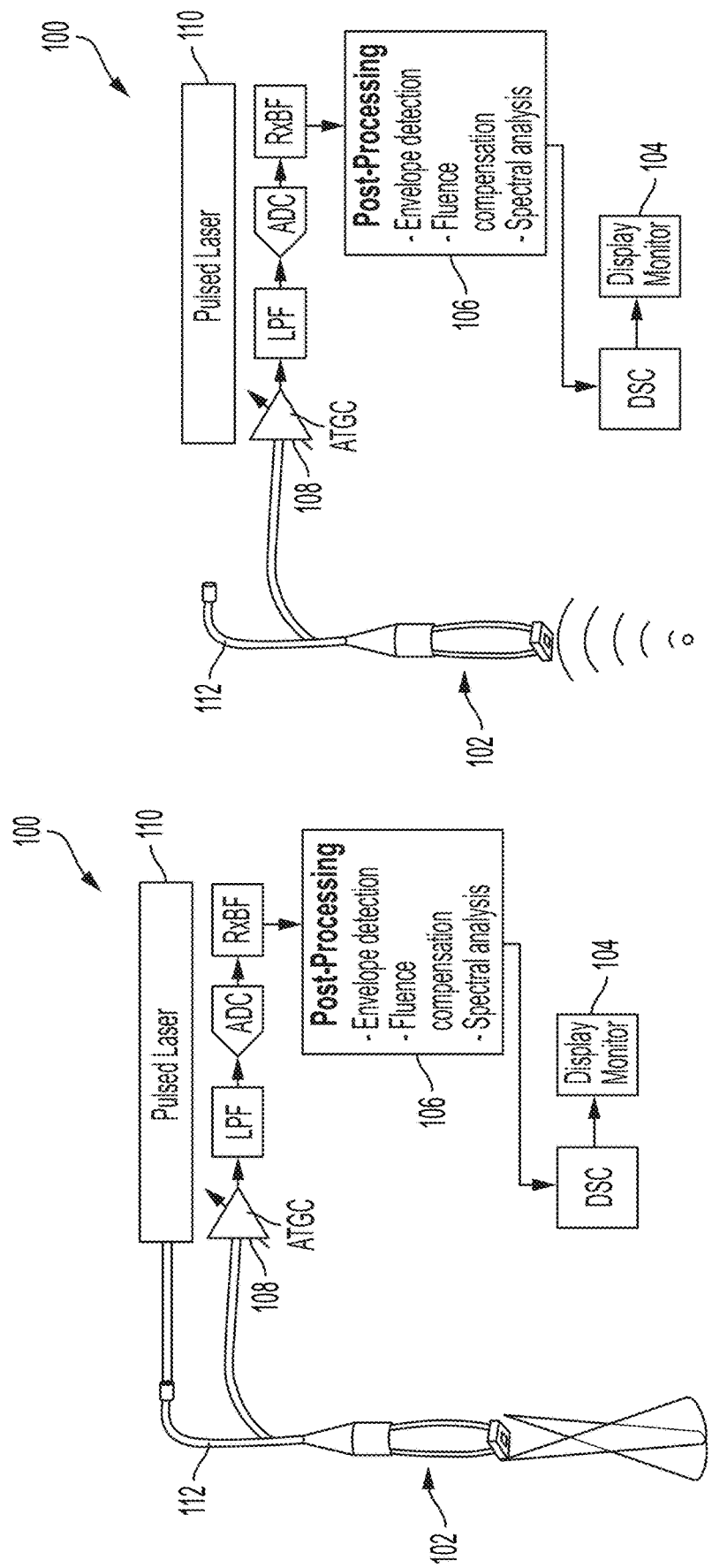

ULTRASOUND, PHOTOACOUSTIC, AND VISCOELASTIC IMAGING SYSTEMS AND METHODS FOR CERVICAL ANALYSIS TO ASSESS RISK OF PRETERM DELIVERY

CROSS-REFERENCE TO RELATED APPLICATIONS

The present disclosure claims the benefit of U.S. Provisional App. No. 62/748,613, filed Oct. 22, 2018, and entitled "ULTRASOUND, PHOTOACOUSTIC, AND VISCOELASTIC IMAGING SYSTEMS AND METHODS FOR CERVICAL ANALYSIS TO ASSESS RISK OF PRETERM DELIVERY," the entirety of which is incorporated by reference herein.

TECHNICAL FIELD

The present disclosure generally relates to multi-modal imaging systems and methods to assess risk of preterm delivery and, more specifically, to ultrasound (US), viscoelastic (VE), and photoacoustic (PA) systems and methods for cervical analysis of an expectant mother to assess risk of preterm delivery of the fetus.

BACKGROUND

Accurate detection of expectant mothers that are at risk of preterm birth of a fetus is a challenging clinical problem. A fetus that is born preterm is born before 37 completed weeks of gestation. Complications from such preterm birth is a leading cause of death of children less than five years of age and is a major cause of an increased risk of a myriad of illnesses and conditions ranging from, and not limited to, chronic respiratory disease, blindness, and neurological disorders.

Use of conventional ultrasound technologies to attempt to detect a risk of preterm birth may utilize US imaging to detect and measure a clinical biomarker of less or equal to than 25 mm of cervical length, which biomarker is indicative of a risk of preterm birth. However, less than 40% of mothers delivering preterm are diagnosed with such a shortened cervix biomarker through such US imaging, which reflects a lack of sensitivity and sensitivity required for more accurate detection of those expectant mothers at risk of preterm birth.

Accordingly, alternative systems and methods to accurately detect a risk of preterm delivery of a fetus are desired.

BRIEF SUMMARY

According to the subject matter of the present disclosure, a system for detection of a risk of preterm delivery may include one or more processors, one or more memory modules communicatively coupled to the one or more processors, an ultrasound machine comprising a display and communicatively coupled to the one or more memory modules, a probe device communicatively coupled to the ultrasound machine, and machine readable instructions stored in the one or more memory modules. The machine readable instructions may cause the system to perform at least the following when executed by the one or more processors: transmit a plurality of (ultrasound) US signals (i.e., waves) and (photoacoustic) PA signals (i.e., safe laser excitation pulses) from the probe device toward a cervix upon insertion of the probe device into a vaginal birth canal of a maternal pelvis, wherein the transmitted PA signals comprise short and safe laser pulses configured to be tunable based on a change in wavelength; receive, into the probe device, a plurality of wave signals including reflected US wave signals, generated VE wave signals through use of the cervix as a VE medium, and generated PA wave signals via the probe device; convert through a transducer of the probe device the plurality of wave signals into a plurality of signals configured to be readable by the one or more processors; transmit, via the probe device, the plurality of signals to the ultrasound machine; generate one or more images of the cervix and information indicative of tissue characteristic information of the cervix derived from and at least partially based on the plurality of signals in real-time; and display the one or more images on the display of the ultrasound machine.

In an embodiment, a system for risk of preterm labor assessment during delivery may include one or more processors, one or more memory modules communicatively coupled to the one or more processors, an ultrasound machine comprising a display and communicatively coupled to the one or more memory modules, and a probe device communicatively coupled to the ultrasound machine. The system may further include machine readable instructions stored in the one or more memory modules that cause the system to perform at least the following when executed by the one or more processors: transmit a plurality of (ultrasound) US and (photoacoustic) PA and viscoelastic (VE) signals from the probe device toward cervical tissue of a cervix upon insertion of the probe device into a vaginal birth canal of a maternal pelvis including a fetus, wherein the transmitted PA signals comprise laser pulses configured to be tunable based on a change in wavelength, wherein the cervical tissue is a medium for the VE signals. The machine readable instructions may further cause the system to perform at least the following when executed by the one or more processors: receive, into the probe device, a plurality of reflected US and PA and VE signals via the probe device, transmit, via the probe device, the received plurality of reflected US and PA and VE signals to the ultrasound machine, generate one or more images and one or more biomarker parameters of the cervical tissue at least partially based on the US and PA and VE signals in real-time, generate a risk parameter of preterm delivery of the fetus based on the one or more biomarker parameters of the cervical tissue, and display the one or more images and the risk parameter on the display of the ultrasound machine.

In another embodiment, a method for multi-parametric, non-invasive, and real-time assessment of a risk of preterm labor for a fetus in a maternal pelvis may include positioning a probe device in the maternal pelvis toward cervical tissue of a cervix of the maternal pelvis, wherein the probe device is communicatively coupled to an ultrasound (US) machine and one or more processors, transmitting a plurality of US and photoacoustic (PA) and viscoelastic (VE) signals from the probe device toward the cervical tissue of the cervix, wherein the cervical tissue is a medium for the VE signals, and receiving, into the probe device, a plurality of reflected US and PA signals via the probe device. The method may further include transmitting, via the probe device, the received plurality of reflected US and PA and VE signals to the US machine, generating one or more images and one or more biomarker parameters of the cervical tissue based on the reflected US and PA and VE signals, generating a risk parameter of preterm delivery of the fetus based on the one or more biomarker parameters of the cervical tissue, and displaying in real-time the one or more images via the US machine.

These and additional features provided by the embodiments described herein will be more fully understood in view of the following detailed description, in conjunction with the drawings.

BRIEF DESCRIPTION OF THE SEVERAL VIEWS OF THE DRAWINGS

The embodiments set forth in the drawings are illustrative and exemplary in nature and are not intended to limit the subject matter defined by the claims. The following detailed description of specific embodiments of the present disclosure can be best understood when read in conjunction with the following drawings, where like structure is indicated with like reference numerals and in which:

FIG. 2 illustrates an example system for implementing computer and software-based methods to utilize the device of FIGS. 1A-1C in a mode to transmit tunable laser pulses as photoacoustic (PA) signals and detect generated ultrasound (US) waves as received PA waves, according to one or more embodiments shown and described herein;

FIG. 3 illustrates the example system of FIG. 2 to utilize the device of FIGS. 1A-1C in another mode to transmit US waves and detect reflected US waves as received US waves, according to one or more embodiments shown and described herein;

DETAILED DESCRIPTION

Figure 1C:
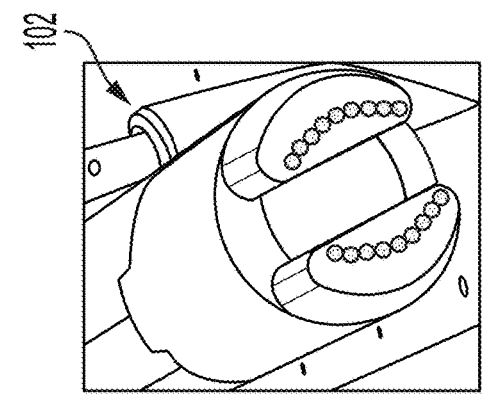
FIG. 1C illustrates an isometric view of the multi-model probe device including the sheath and the arrangement.

The present disclosure relates to systems and methods to optimize clinical care of a fetus and mother to assess a risk of preterm delivery through use of a multi-model probe to image a cervix through a vaginal canal and generate multimodal imaging providing a variety of cervix tissue characteristic data. The systems and methods described herein further permit a visualization of cervix tissue to determine oxygen saturation with respect to the cervix tissue.

Due to a lack of a highly sensitive and accurate diagnostic modality to predict the risk of preterm delivery, preterm delivery is a main cause of perinatal morbidity and mortality worldwide, which is associated with a significant healthcare cost spent on prematurity. Although measurement of cervical length by transvaginal ultrasound has assisted to guide diagnosis and management of preterm delivery, such technology alone fails to capture a majority of preterm deliveries that occur. The multi-modal imaging tool as described herein acquires additional data on functional and molecular composition of the cervical tissue (e.g., collagen organization and water content) to better identify and detect patients at risk of preterm delivery at improved rates over US systems depending on cervical length measurement alone. In embodiments, spectroscopic photoacoustic imaging is utilized with the probe device described herein to measure important cervical tissue parameters including, but not limited to: (a) collagen organization (collagen/water ratio), (b) tissue hydration (water content); (c) tissue oxygenation; and/or (d) tissue vascularity (hemoglobin content).

A method for imaging of cervical tissue is described herein that utilizes a single instrument to acquire multi-parametric images of morphologic, functional, biomechanical, and/or molecular composition of cervical tissue, including, but not limited to, collagen disorganization and tissue hydration. Use of such a multi-model imaging device enables a study of the correlation of each individual parameter as a respective biomarkers, and the combination of these parameters, with the incidence of preterm delivery. Further as described herein, PA imaging is one of the multi-modal operations utilized to evaluate collagen disorganization and tissue hydration (ratio of collagen-to-water content) in cervical tissue.

In an expectant mother about to under preterm delivery that may not have been detected by a shortened cervix length, the cervix may undergo functional and molecular structural changes that weaken its strength to hold the pregnancy before the onset of shortening in length. In addition, the length of the cervix may not represent its collagen content or strength. The multi-modal device and system described herein is a reliable, clinically translatable, and non-invasive diagnostic modality capable of acquiring information about cervical ripening beyond anatomical and structural parameters. Such a multi-modal imaging tool is configured to acquire multi-parametric data on functional and molecular composition of the cervical tissue (e.g., collagen disorganization and water content) to better identify patients at risk of preterm delivery as described herein. The multi-modal imaging tool is configured to combine US, PA, and/or VE imaging modalities to generate a spectrum of structural, molecular, and/or biomechanical biomarkers representing cervical remodeling and thus aids to increase sensitivity and to reduce a false-positive rate in detecting patients at risk of preterm delivery compared to US scans and cervical length analysis alone. A multi-modal probe that includes a transvaginal US transducer is configured to acquire, with respect to cervical tissue, advanced US information as microstructural biomarker information, PA information as functional and molecular biomarker information, and VE information as biomechanical biomarker information of the cervical tissue. The imaging device and system described herein assist to achieve a reliable screening/diagnosis with high specificity to detect early signs of cervical insufficiency that can lead to preterm delivery without increasing risk to the fetus or mother, causing additional discomfort, or significantly increasing a scanning time of the expectant mother.

Figure 11:
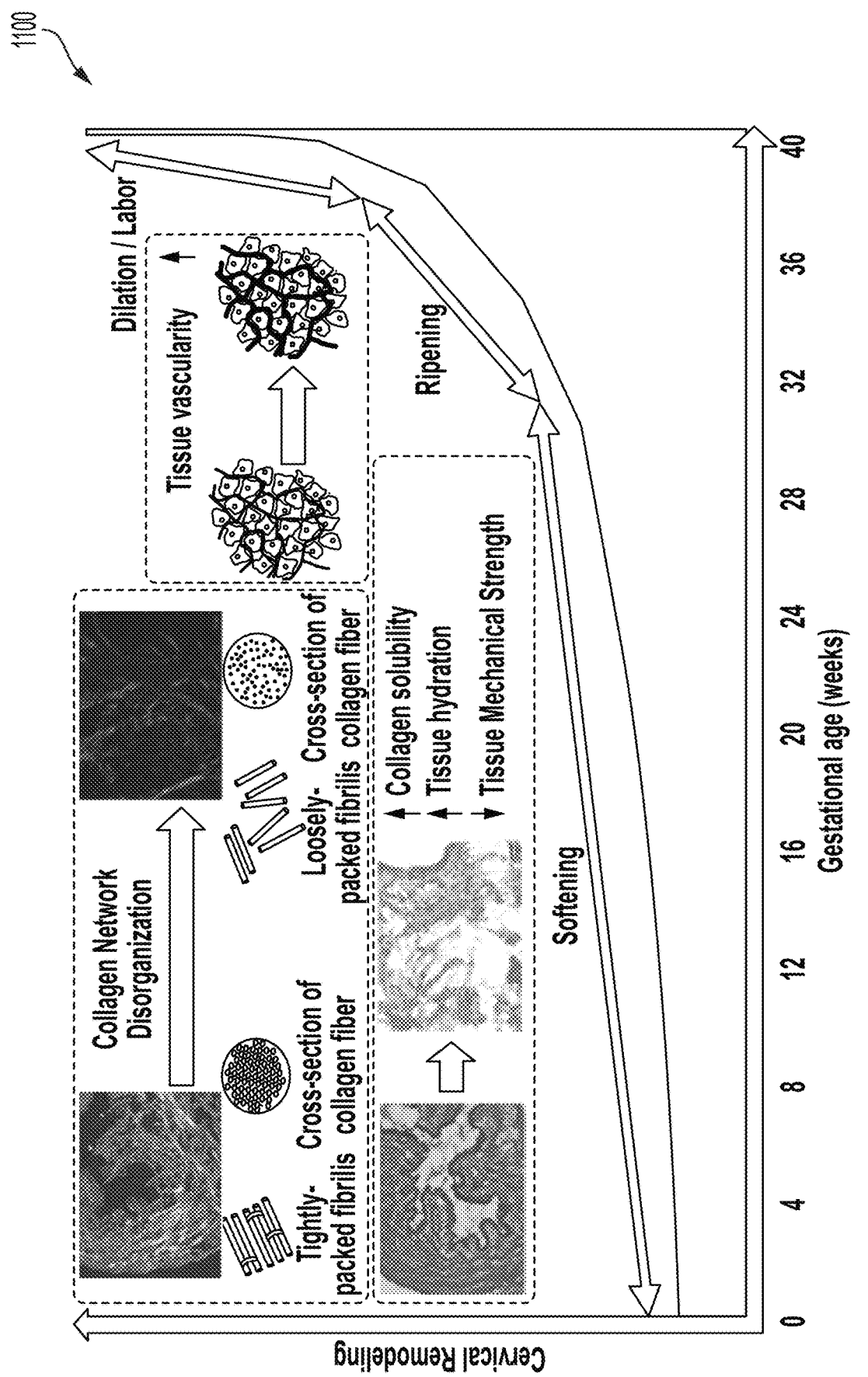
FIG. 11 schematically illustrates a graphical chart indicative of dynamic cervix tissue changes through pregnancy.

Referring to a chart 1100 of FIG. 11, structural cervical weakness leads to cervical insufficiency that is a main cause of preterm delivery. Many expectant mothers are identified to have a normal cervical length at 18-24 weeks of gestation but yet still develop a short cervix and deliver preterm in a true-positive case. The multi-modal imaging systems and devices as described herein provide for more than simply a cervical length analysis through US imaging and provide a variety of additional biomarker data with respect to cervical tissue through multi-modal imaging that assists to detect a risk of preterm delivery even where a cervical length is not yet shorted and would otherwise be undetected. For example, US imaging may provide biomarker information such as cervical length, tissue anisotropy, and microstructural information of the cervical issue, VE imaging may provide tissue biomechanical information such as elasticity and viscosity of the cervical tissues as described below, and PA imaging may provide functional and molecular composition biomarker information such as vascularity, tissue oxygenation, hydration, and collagen content of the cervical tissue.

Cervix tissues changes dynamically through pregnancy, affect more parameters than cervical length, such as, but not limited to, a collagen network in the tissue, vascularity, mechanical biomarkers, and microstructural aspects of the tissue. The ripening of the cervix over gestation involves a gradual change in consistency from hard to medium to soft, which is currently described by a measurement of Bishop score as understood to those of skill in the art, and is able to be obtained by digital examination. The cervical remodeling process during gestation depends on an increase in water content and remodeling of the tissue's collagen network in an extracellular matrix. Transvaginal US systems are typically utilized as a single modality system to monitor the cervix by measuring cervical length. The multi-modal systems and devices described herein combine US, PA, and VE imaging into an integrated multi-modal technique to enable the acquisition of additional potential biomarkers related to the cervical tissue, such as functional, molecular, and mechanical biomarkers, which can aid in detecting cervical changes at a more real-time rate during pregnancy to assess the risk of preterm delivery even where cervical length has not yet changed.

Figure 1B:
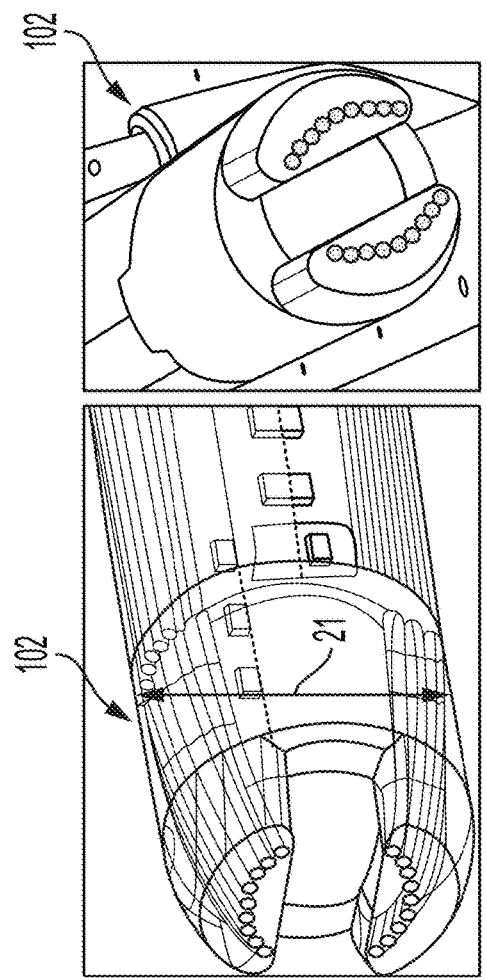
FIG. 1B illustrates an isometric view of a sheath of the multi-modal probe device to house the arrangement of FIG. 1A.
Figure 1A:
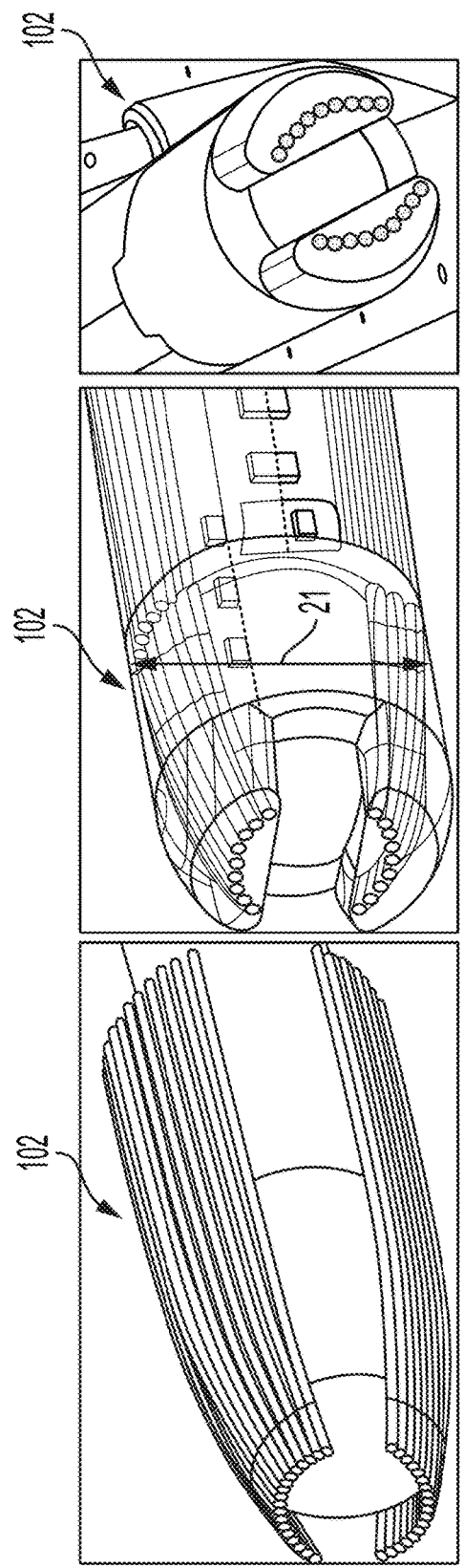
FIG. 1A illustrates an isometric view of an arrangement of an internal transducer and fiber optics assembly of a multi-modal probe device to assess risk of preterm birth, according to one or more embodiments shown and described herein.

Referring initially to FIGS. 1A-1C, a multi-modal probe device 102 is illustrated for assessment of risk of preterm delivery as described herein. By way of example, and not as a limitation, the probe device 102 may be one as described in U.S. Publ. No. 2018/0214119 to Mehrmohammadi et al., entitled "Ultrasound and Photoacoustic Systems and Methods for Fetal Brain Assessment During Delivery," filed Jan. 26, 2018, as assigned to Wayne State University and incorporated by reference herein in its entirety.

For example, the probe device 102 includes a sheath including a fiber holder that has a plurality of openings sized and shaped to receive corresponding fibers of a fiber assembly. The sheath of the probe device 102 includes an opening sized and configured to receive a transvaginal, ultrasound (US) transducer, which includes an active surface. As a non-limiting example, the US transducer may be a curved-array transducer with a frequency range bandwidth of about 5 MHz to about 9 MHz, such that pulses of a frequency in the range may be emitted from an array of about 128 transducer elements. Other forms of light delivery such as fused fibers (to a customized shape) may also be incorporated into the sheath for light delivery.

US waves are transmitted in a non-ionizing manner through the active surface of the US transducer of the probe device 102, which is communicatively coupled to an US machine. As a non-limiting example, the US probes may be high-frequency probes. The active surface of the US transducer collects the sound waves that reflect and bounce back from tissue to create images from the sound waves received through the active surface. For example, the US transducer records changes in a pitch and direction of the bounced-back acoustic waves to measure and display these waves as a real-time image on a monitor of a computer or US machine, for example. In embodiments, the plurality of US signals are transmitted from the active surface of the probe device as a series of sound wave signals, and the plurality of PA signals are transmitted from the optical fiber assembly as a series of laser pulse signals from the laser.

The fiber holder is sized and configured to contain a fiber assembly including a plurality of optical fibers for use in photoacoustic (PA) imaging. The fiber assembly may be formed of fused fiber bundles made of flexible small core silica optical fibers that are fused on proximal and distal ends to create highly flexible fiber bundles that are efficient in transporting laser energies. In PA imaging, non-ionizing laser pulses and/or radio-frequency (RF) pulses may be used (as in thermoacoustic imaging) and are delivered to biological tissue, and a portion of the delivered energy is absorbed into the tissue and converted to heat that leads to a transient thermoelastic expansion and wideband ultrasonic emission. The US transducer detects the generated ultrasonic waves that are analyzed to produce images. Optical absorption through PA imaging is associated with physiological properties such as hemoglobin concentration and oxygen saturation. The PA signal (i.e., the magnitude and/or frequency of the ultrasonic emission) is proportional to a local energy deposition to reveal physiologically specific optical absorption contrast and thus assist to form 2D or 3D images of targeted areas. As blood typically has higher absorption in order of magnitude than surrounding tissue, a sufficient endogenous contrast exists for PA imaging to visualize blood vessels.

Further, the optical absorption in tissue may be due to endogenous molecules such as hemoglobin. Hemoglobin is an iron-containing oxygen-transport metalloprotein in red blood cells which carries oxygen from respiratory organs to the tissues of the rest of the body where oxygen is released to permit aerobic respiration and provide metabolic energy. Oxy-hemoglobin refers to hemoglobin saturated with oxygen, and deoxy-hemoglobin refers to hemoglobin desaturated with oxygen. Thus, as the absorption spectra of oxy-hemoglobin and deoxy-hemoglobin differ, the difference is able to be used for a measurement of an amount of oxygen in targeted blood vessel to, for example, determine an oxygen saturation measurement.

Figure 1D:
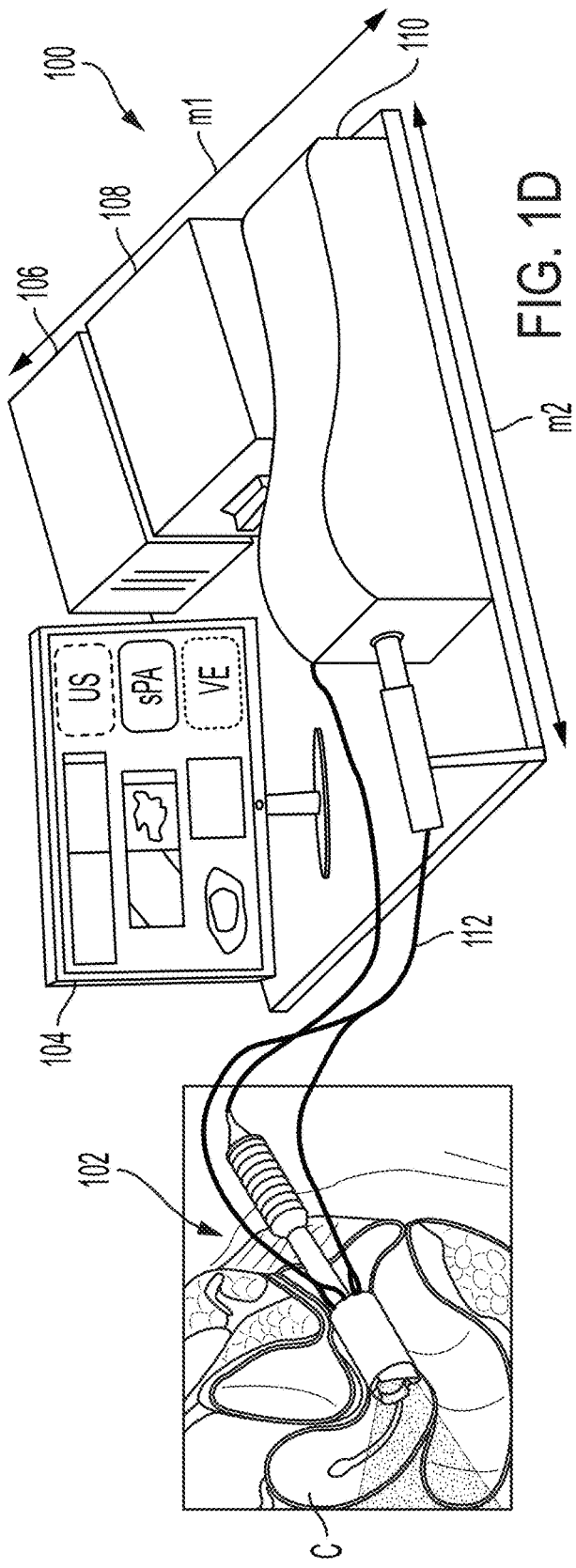
FIG. 1D illustrates a system for using the multi-model probe to image a cervix of an expect mother to assess a risk of preterm birth, according to one or more embodiments of the present disclosure.

An imaging system 100 is shown in FIGS. 1D and FIGS. 2-3. FIG. 1D is representative of the structural components, FIG. 2 is representative of use of the imaging system and associated electronic components to produce and analyze photoacoustic signal, and FIG. 3 is representative of use of the imaging system and associated electronic components to produce and analyze an ultrasound signal. As shown with respect to an imaging system 100 in either FIG. 1D or FIGS. 2-3, the probe device 102 is communicatively coupled to a US machine to monitor and measure oxygenation and other cervical tissue characteristics as described in greater detail herein through utilizing information obtained by transvaginal US (TVUS) imaging (such as structure and movement of the blood vessels in the cervix due to real-time US image capture) in combination with oxy-hemoglobin and deoxy-hemoglobin concentrations obtained by PA imaging to provide real-time measurements of cervical tissue characteristics that may be used to assess a risk of preterm delivery based on cervix tissue degradation, such as a detection of a decreased collagen to water ratio as described in great detail further below. As additionally described in greater detail further below, the probe device 102 is configured to operate in a multi-modal manner to provide US, PA, and viscoelastic (VE) imaging of, for example, a cervix C of an expectant mother.

As a non-limiting example, US and PA signals are transmitted from the probe device 102 toward the cervix C of the expectant mother through the vaginal canal. Reflected US waves and PA signals (as US waves generated from optical absorption by the tissue of laser light as described below) are received back into the probe device, which converts the waves into signals readable by a processor and transmits the converted signals to a US machine for processing 106, such as through a digital system controller (DSC), and to display 104 one or more images. An interleaved (and overlaid) image of the cervix is generated at least partially based on the US, PA, and VE signals in real-time. For example, transmitted US signals may be in the form of US wave pulses, and transmitted PA signals may be in the form of tunable laser pulse signals. The post-processing may determine an envelope detection of an envelope surrounding extremes of the generated digital signals, fluence compensation to compensate a fluence decay in an original three-dimensional PA map of the actual imaging, and a spectral analysis of the digital signal to generate the spectroscopic photoacoustic (sPA) imaging.

The probe device 102 as inserted is thus able to be used for PA imaging through the fiber assembly and for US imaging through use of the active surface of the US transducer to provide one or more images of the cervix of the expectant mother. The multi-modal probe as described herein may be used as part of a tri-modal, US/PA/VE probe and imaging system 100 including a transvaginal US transducer, which may be an 128-element curved linear array transducer for operation at 5-9 MHz and including a diameter of approximately 19 mm. The multi-modal problem may also have a light delivery system including a bundle of large core-size fibers, such as 19 multimode fibers of 1000 μm (i.e., 1 mm) core size, and a numerical aperture (NA) of=0.39. Of the 19 fibers of such a probe, 18 may be used to deliver light to the vicinity of the US transducer, and one fiber may be used for real-time energy monitoring. To protect the fibers and adjust their locations, a fiber-holding sheath may be utilized such that a total diameter of the US/PA/VE probe may be 29.2 mm. The fibers may be bent close to the tip of the fiber to enhance an illumination pattern. A performed Monte-Carlo model simulation may be utilized to compare an angled (bent) fiber versus the straight fiber alignment around the transvaginal US probe. The cervical tissue's scattering properties make a negligible difference in the light propagation pattern when the probe is assumed to be in contact with the tissue surface. However, for those scenarios in which the probe is at a distance from the tissue's surface, angled fibers with a focal plane at a certain distance (such as 25 mm) from the transducer could have a better light propagation pattern due to better matching between the illumination patterns with an elevational focus of the US transducer. A proximal end of the fiber bundle 112 may be coupled to a self-cooled, nanosecond, tunable pulsed laser 110, such as one commercially available as Phocus Core by OPOTek® Inc., which may be tunable across a range of wavelengths between 680 nm to 2500 nm at pulse repetition of 10 Hz. A programmable digital US acquisition system 108, such as one commercially available as Vantage 128 by Verasonics®, Inc., may be utilized to acquire multi-modal images such as US, PA and VE images. The programmable digital US acquisition system 108 may include a filter system as shown in FIGS. 2-3 including an analog time gain compensation (ATGC) signal receiver, a low-pass filter (LPF), an analog to digital converter (ADC), and a receive beamformer (RxBF) to perform receive beamforming on a digital signal to produce a signal that represents echo characteristic of tissue that correspond to a desired depth of imaging. A custom-built, high speed field-programmable gate array, which may be a 200 MHz, BASYS 3 FPGA commercially available from Digilent Inc., may be used to synchronize laser excitation and US acquisition as well as to control interleaved acquisition of US and PA frames, followed by acoustic radiation force (ARF)-generated shear wave speed maps. Interleaved US, PA, and VE images may be reconstructed using an adaptive beamforming algorithm.

A real-time US/PA imaging sequence may acquire a plurality of US frames, such as five, plane-wave frames at 21 compounding angles between two consecutive PA frames, and then may be followed by VE imaging. All synchronization signals may be calibrated, and co-registered US/PA/VE images may be reconstructed. In addition, as characterized by an imaging of a calibration phantom during experimentation as described herein, an imaging axial resolution may be set at 260 µm and lateral resolution at 25 mm may be set at 450 µm.

Figure 8:
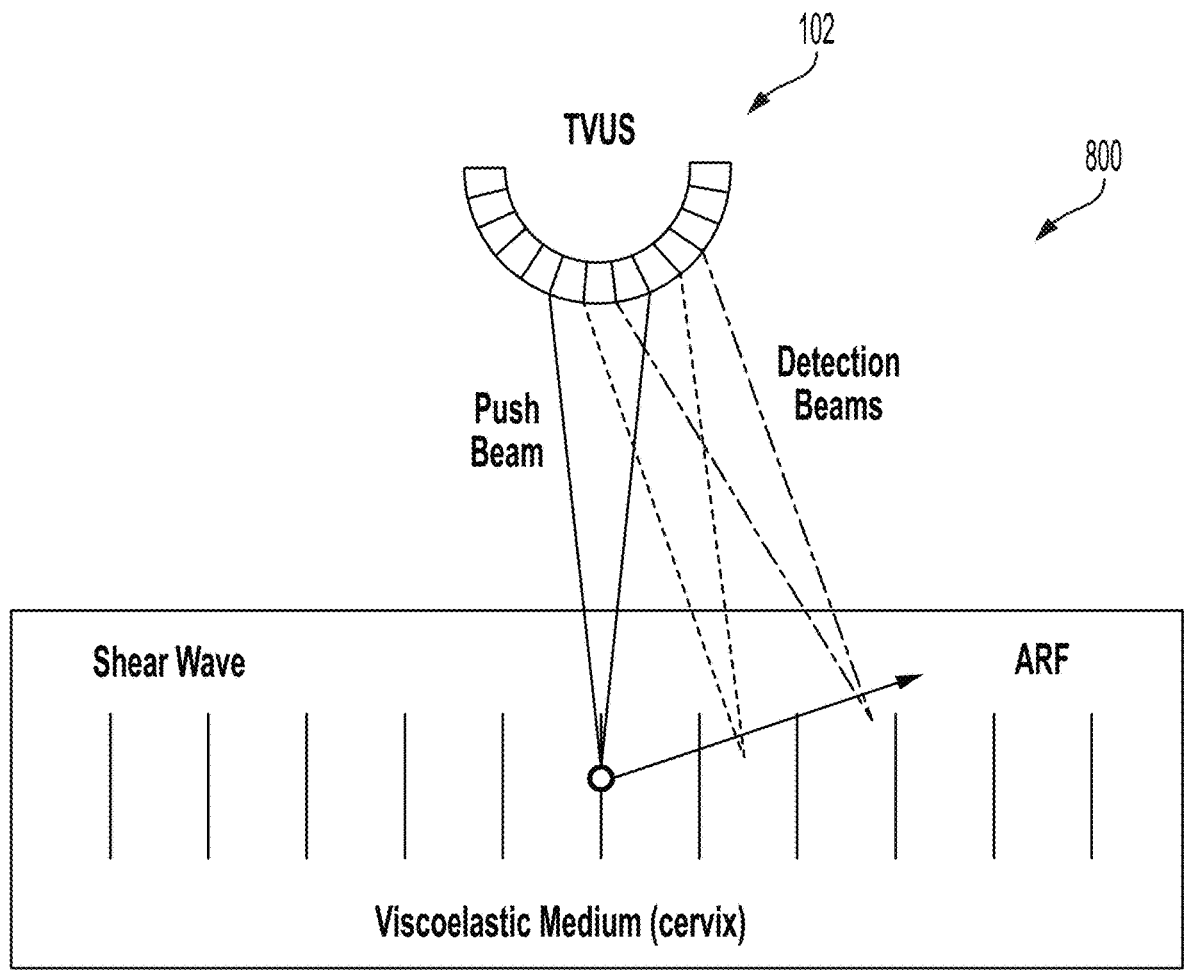
FIG. 8 schematically illustrates a system to utilize the device of FIGS. 1A-1C in a viscoelastic (VE) mode with a cervix as a VE medium, according to one or more embodiments shown and described herein.
Figure 9:
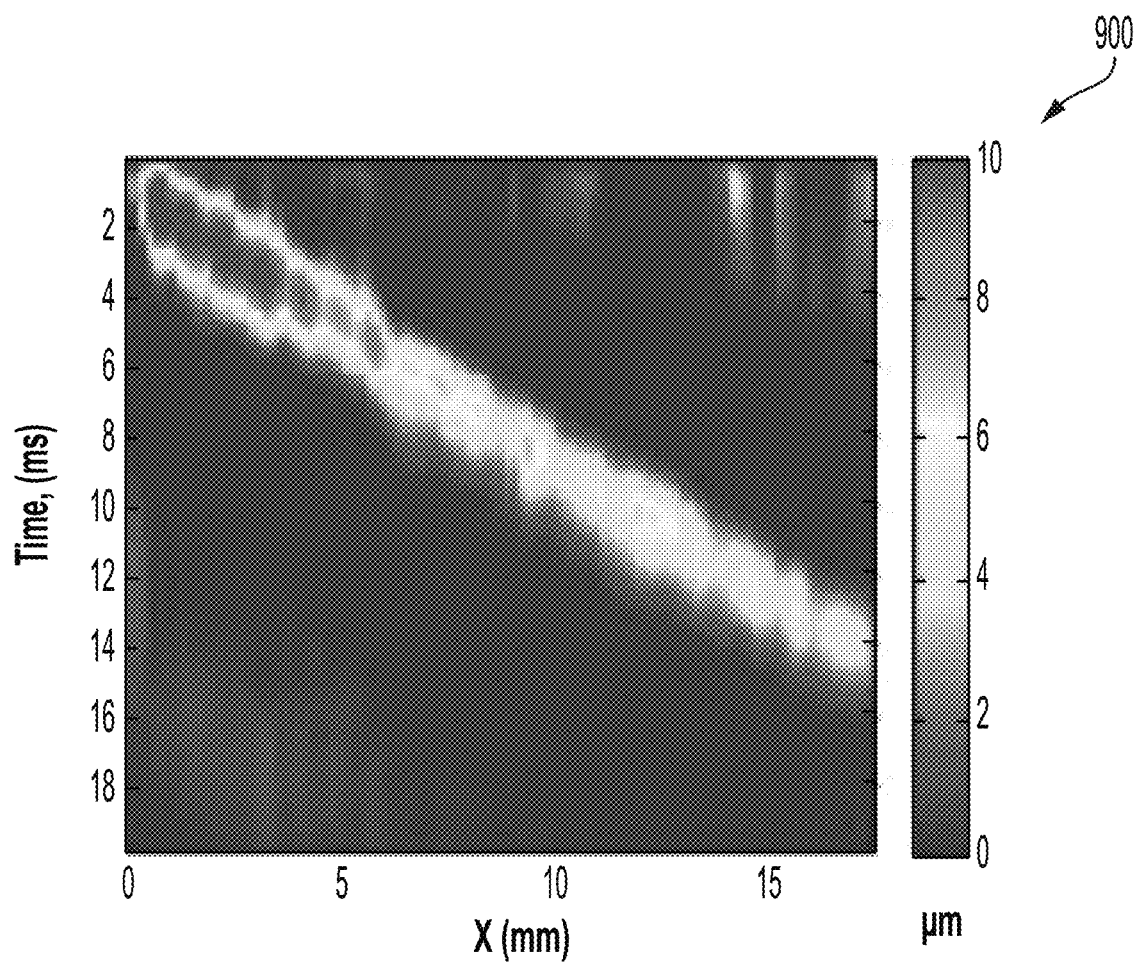
FIG. 9 illustrates a VE image illustrating a time-space displacement measured from the VE system of FIG. 8.
Figures 10A, 10B:
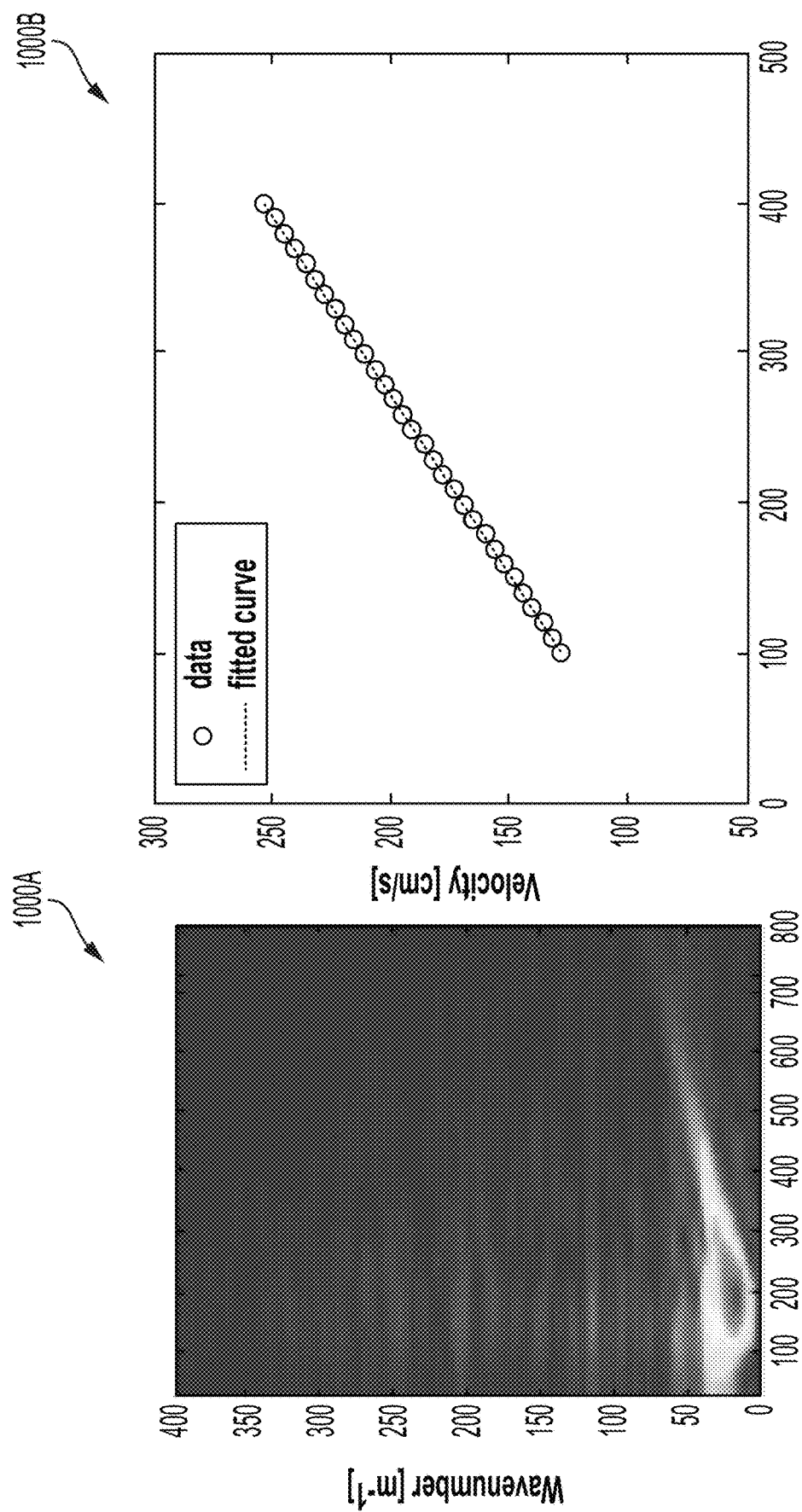
FIGS. 10A-10B respectively illustrate a wave number frequency domain and example model for a viscoelastic medium derived from the VE system and FIG. 8 and VE image of FIG. 9.

Referring to FIGS. 8-10 with respect to VE imaging, FIG. 8 schematically illustrates a system 800 to utilize the device as the transvaginal ultrasonic (TVUS) prob 102 of FIGS. 1A-1C in a viscoelastic (VE) mode with a cervix as a VE medium, FIG. 9 illustrates a VE image 900 illustrating a time-space displacement measured from the VE system 800 of FIG. 8, and FIGS. 10A-10B respectively illustrate (i) a wave number frequency domain and (ii) an example model for a viscoelastic medium derived from the VE system 800 of FIG. 8 and VE image 900 of FIG. 9. In particular, VE imaging is able to provide cervical tissue biomechanical values such as elasticity and viscosity of the image cervical tissue of an expectant mother, where the cervix acts as the viscoelastic medium. Such imaging builds upon shear wave elastography (SWE) that provides quantitative methods of a tissue's biomechanics, but that otherwise ignores shear viscosity, which is not ignored by the multi-modal systems and algorithms as described herein. As a non-limiting example, the probe device described herein may provide an ARF push of 100-600 µs and an image frame rate of 2,000-10,000 frames per second (fps). With respect to SWE, a Young Modulus (i.e., Elastic Modulus) of tissue is measurable as $\mu_1 = \rho C_s^2$, where $C_s$ is representative of a shear wave propagation speed. However, SWE ignores the tissue viscosity, or rather shear viscosity value, of $\mu_1$ in its evaluation. In particular, Equation X below shows that $$C_s = \sqrt{\frac{2(\mu_1^2 + \omega^2 \mu_2^2)}{\rho\left(\mu_1 + \sqrt{\mu_1^2 + \omega^2 \mu_2^2}\right)}}$$ (Equation 1A)

With respect to Equation 1A, $\mu_1$ and $\mu_2$ are respectively representative of shear elasticity and shear viscosity. SWE ignores the shear viscosity value of $\mu_2$, as it may otherwise have presented an unwanted bias on measuring elastic modulus. However, this resulted in an important input of shear viscosity as biomechanical information that is missing from the overall biomarker analysis. The multi-modal imaging systems and devices with VE imaging as described herein are capable of providing for analysis of shear viscosity as biomechanical information of cervical tissue of an expectant mother through shear wave dispersion vibrometry (SDUV) as depicted in FIGS. 8-10, which utilizes SWE data acquisition in addition to post-processing functionality available through SDUV to provide the shear viscosity value of $\mu_2$ of cervical tissue for VE imaging analysis of cervical tissue data as well as the shear elasticity analysis of $\mu_1$. FIG. 10 illustrates graphical results showing a wave number frequency domain and a model, such as the Kelvin-Voigt model for a VE medium, as derived from use of the multi-modal imaging system utilizing VE imaging as described herein to generate a more robust elastic modulus analysis of the cervical tissue than otherwise available through SWE.

Additional experimentation, as captured in TABLE 1 below, illustrated that tissue-mimicking gels as different concentrations resulted in different viscoelastic properties. An acquisition time for each frame including transfer of data to a host computer was 10 ms, and post-processing and the Voigt model was used to extract $\mu_1$ and $\mu_2$.

TABLE 1

|  | Phantom (X% gelatin W/W) | |
| --- | --- | --- |
|  | 10% | 15% |
| Measured $\mu_1$ (transvaginal transducer) - kPa | 3.1 ± 0.2 | 5.21 ± 0.25 |
| Measured $\mu_2$ (transvaginal transducer) - kPa | 1.25 ± 0.18 | 1.9 ± 0.3 |
| Reported $\mu_1$ - Pa · s | 3.30 | 5.37 |
| Reported $\mu_2$ - Pa · s | 1.43 | 2.14 |

Figure 4:
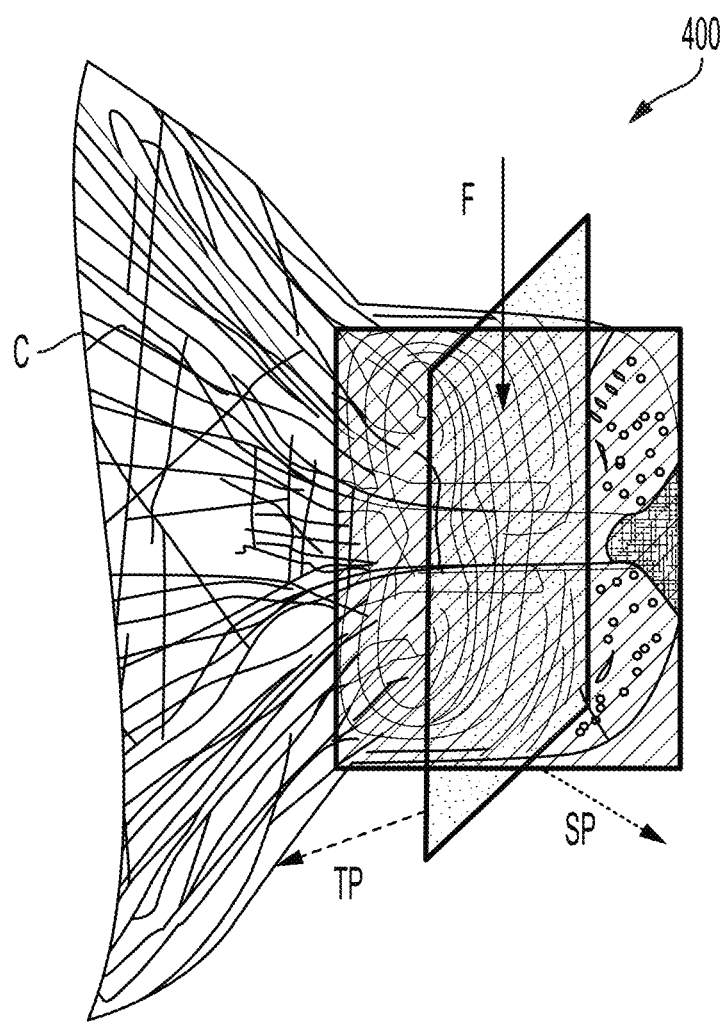
FIG. 4 schematically illustrates imaging of tissue fibers of a cervix across two orthogonal planes, according to one or more embodiments shown and described herein.

Referring to FIG. 4, multi-modal imaging as described herein may be applied to tissue fibers F of a cervix C across two orthogonal planes. The cervical fibers F form a circumferential fiber orientation in a uterine cervix C. A first plane includes a sagittal plane SP such that that the imaging is directed across (i.e., perpendicular to) the fibers F, a second plane includes a traverse plane TP such that the imaging is directed along (i.e., parallel to) the fibers F. The multi-modal imaging systems as describe herein may be utilized to conduct a bi-planar US imaging of the cervical microstructure. For example, a human cervix is a muscular structure that contains collagen fiber oriented mostly in a circumferential pattern, as shown in FIG. 4, where collagen fiber direction is generally circumferential in a dominant outer radial zone. Such an orientation of the collagen fibers introduces anisotropic microstructural features in US imaging of the cervix, and US imaging of cervical tissue microstructure is able to identify tissue anisotropic features, such as an assessment of myocardial fiber structure through imaging at multiple orientations (planes). As determined by the inventors of the present disclosure, degradation of the collagen network during cervical ripening turns an anisotropic muscular cervix into an isotropic (i.e., less muscular) tissue. This degradation and change into isotropic issue implies that the cervical remodeling, especially the degradation of the collagen network in muscular tissue, may potentially be assessed by analyzing acoustic properties of acquired images at more than one plane. Thus, the multi-modal imaging system as described herein is configured to image the cervix at two orthogonal sagittal and transverse imaging planes SP, TP (FIG. 4) to compare the acoustic properties across each plane to evaluate the tissue anisotropy, thus tissue muscularity. Acoustic features such as backscattering power spectrum (BSP), backscattering coefficient (BSC), acoustic attenuation (AA), effective scatterer diameter (ESD), and/or effective acoustic concentration (EAC) may be measured from such acquired RF data from the multi-modal imaging system as described herein. In addition, image-based features of a grayscale B-mode US image may be used to calculate echogenicity of a medium. Different methods may be used to quantify the echogenicity of the medium, such as gray level histogram width (GLHW), mean gray-level (MGL), and gray-level standard deviation (GLSD). GLHW represents histogram distribution of pixel gray-levels within a selected region of interest (ROI), while MGL and GLSD represent the mean and standard deviation of the gray-level values. Echogenicity parameters as robust indicators of tissue acoustic characteristics may distinguish pathological changes, and the echogenicity in US images acquired at multiple planes as describe herein may reveal anisotropic structures (e.g., muscle fibers) and their orientation. Therefore, a difference between echogenicity of the cervical tissue imaged at two orthogonal planes, as in FIG. 4, may be able to differentiate between a collagenous and a ripened cervix that is, for example, more at risk of preterm delivery.

Thus, in embodiments, the plurality of US and PA signals are transmitted from the probe device toward the cervical tissue to generate a sagittal plane view and a transverse plane view orthogonal to the sagittal plane and to generate a collagen degradation parameter as one of the one or more biomarker parameters based on a comparison of the sagittal plane and the transverse plane. The comparison of the sagittal plane and the transverse plane is indicative that the collagen degradation measured over a period of time comprises a risk collagen degradation metric above a predetermined threshold representative of a cervical ripening to turn an anisotropic muscular cervix into a less muscular isotropic cervix, and the risk parameter is indicative of a risk of preterm delivery based on the risk collagen degradation metric.

Figure 5:
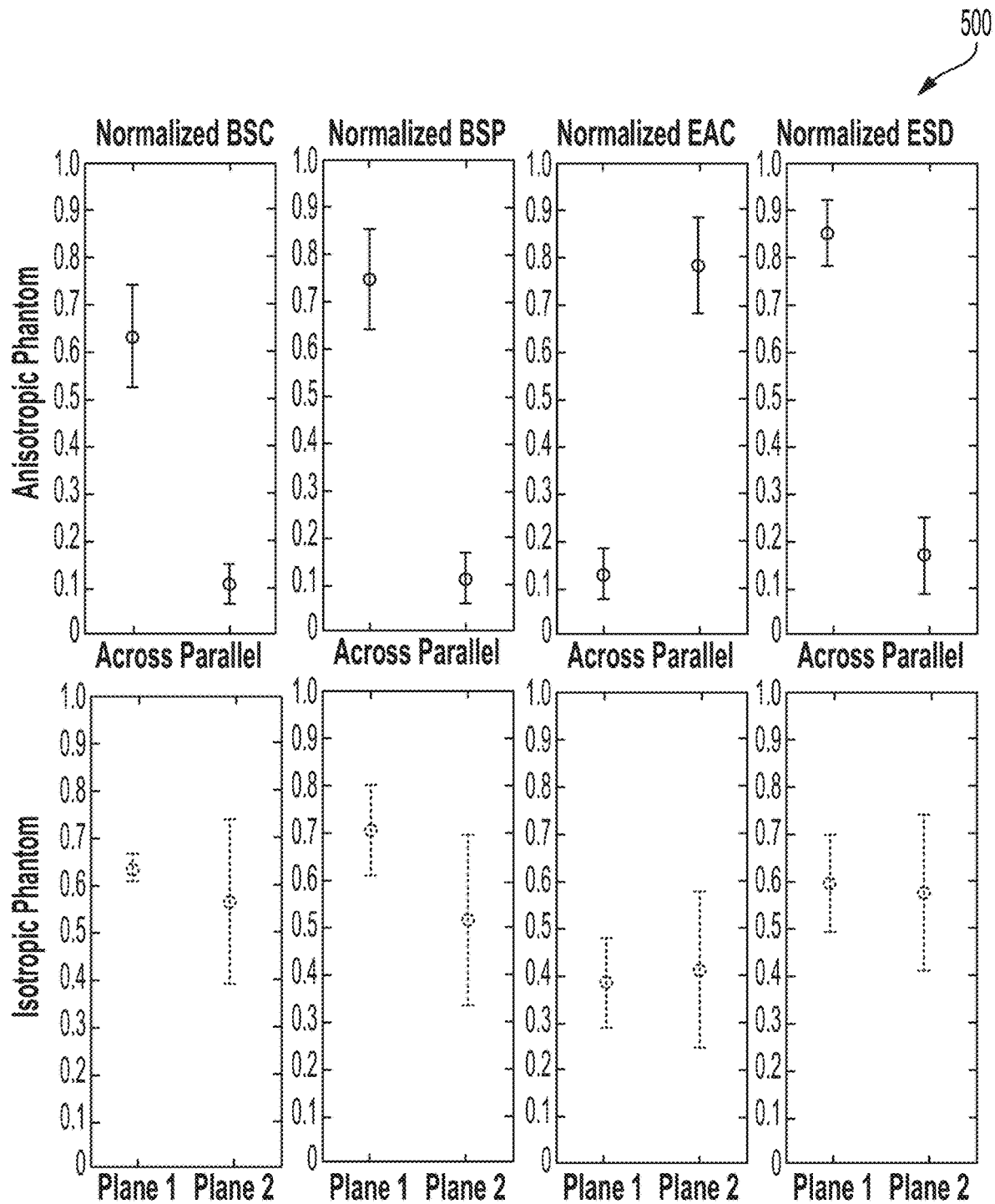
FIG. 5 illustrates graphical depictions of acoustic signatures of imaging with respect to the planes of FIG. 4, including imaging across the fibers and parallel to the fibers in an anisotropic (muscular) phantom and in an isotropic (less muscular) phantom.
Figure 6:
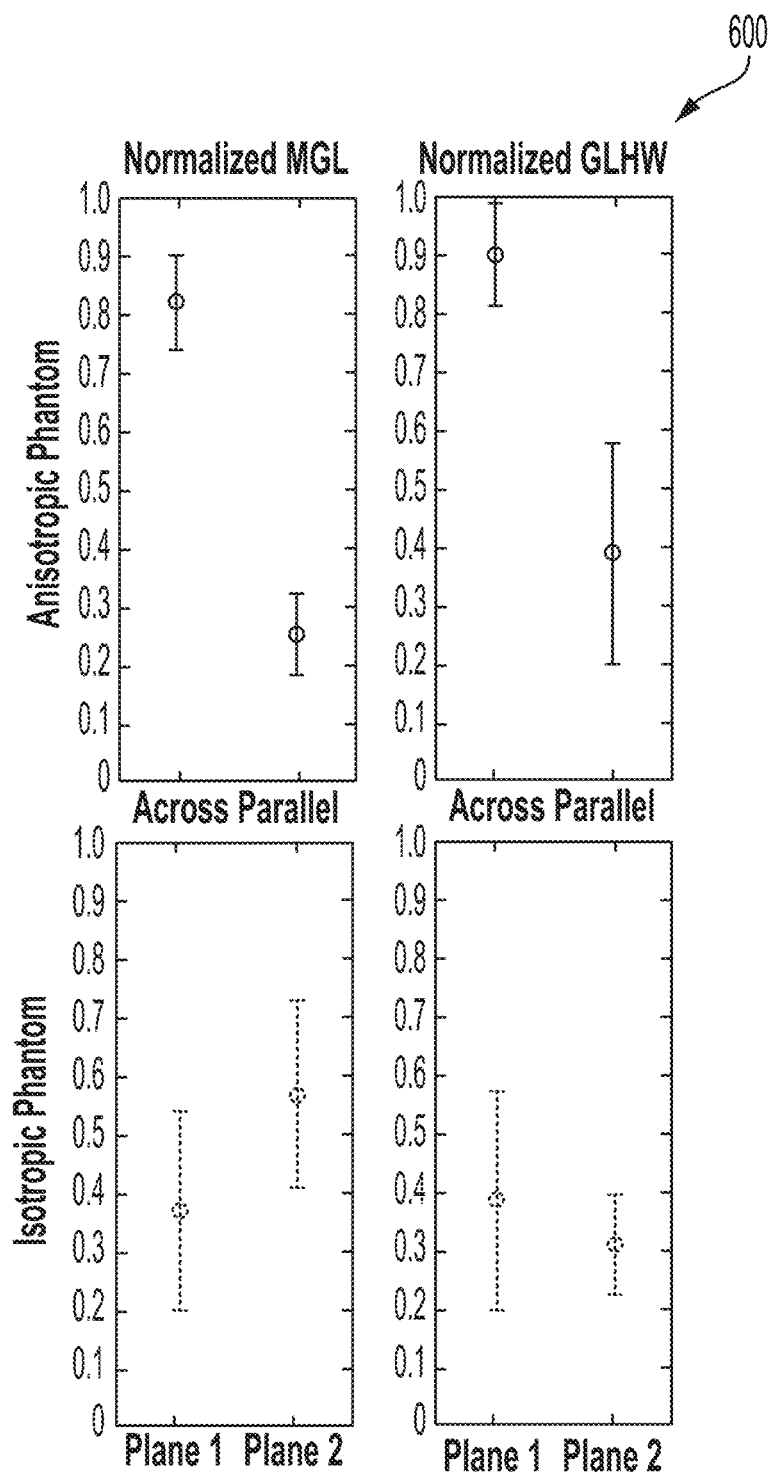
FIG. 6 illustrates graphical depictions of imaged based features of US images with respect to the planes of FIG. 4, including imaging across the fibers and parallel to the fibers in an anisotropic (muscular) phantom and in an isotropic (less muscular) phantom.
Figure 7:
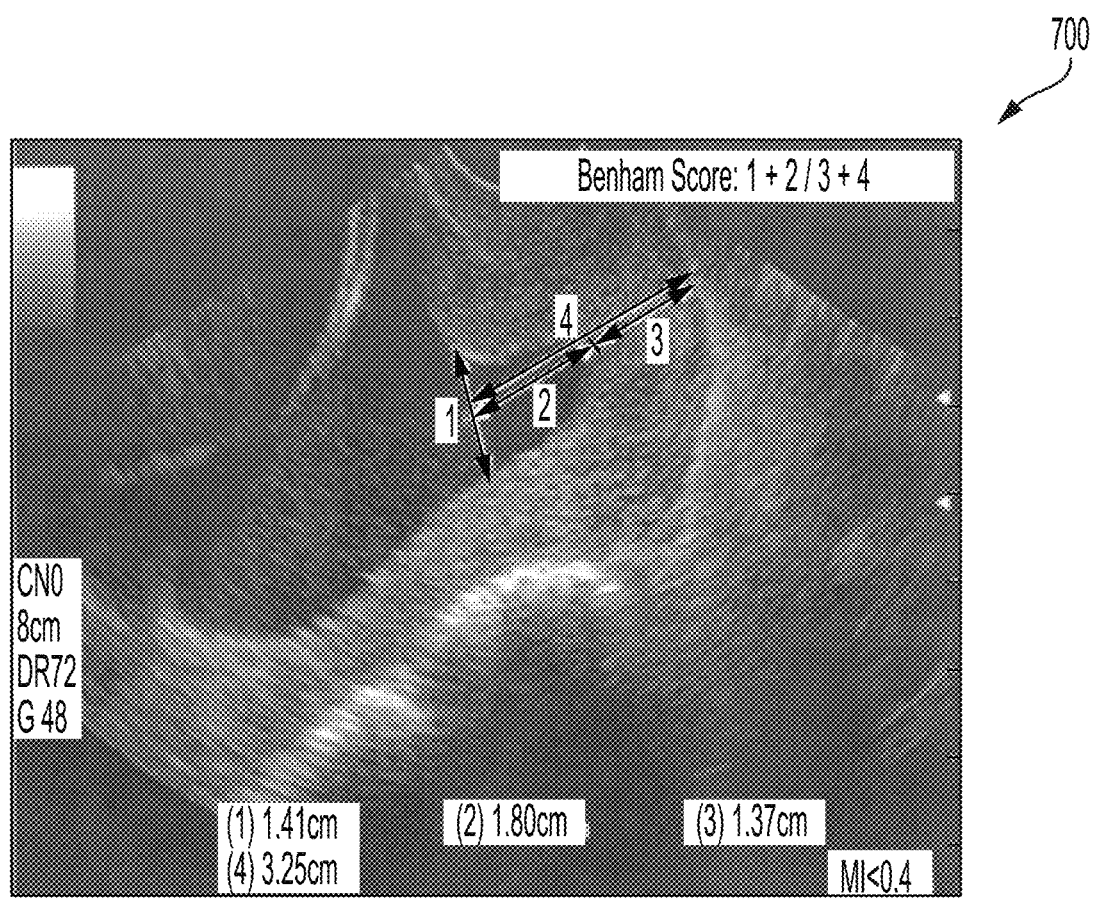
FIG. 7 illustrates an example US image and a measurement of cervical length.

Referring to FIGS. 5-6, FIG. 5 illustrates graphical depictions 500 of acoustic signatures of imaging with respect to the planes of FIG. 4, and FIG. 6 illustrates graphical depictions 600 of imaged based features of US images with respect to the planes of FIG. 4, including imaging across the fibers and parallel to the fibers in an anisotropic (muscular) phantom and in an isotropic (less muscular) phantom. Further, FIG. 7 illustrates an example US image 700 and a measurement of cervical length.

In particular with respect to FIGS. 5-6, a set of experiments was conducted to evaluate the US microstructure imaging of tissue anisotropy with the imaging systems and devices as described herein. The set of experiments on tissue and tissue-mimicking phantoms was performed on an anisotropic phantom made of porcine gelatin with a fibrous structure consisting of 100-μm fibers aligned in a determined orientation and a homogenous, non-fibrous isotropic gelatin/cellulose phantom. Acoustic and image-based features explained above were calculated in two imaging planes, the first plane being along the and the second plane being across the fibers, in anisotropic phantom and in two random orthogonal planes in the isotropic phantom (FIG. 5). Results in the anisotropic phantom revealed a clear difference between the acoustic (FIG. 5) and image-based (FIG. 6) features of US images when the images were acquired parallel to and across the fibers. By contrast, for a homogenous isotropic phantom, no significant difference between images acquired at two orthogonal planes was observed. Similar experiments were performed on bovine muscle tissue samples and bi-planar US imaging results were able to determine the orientation of the fibers within the muscles based on detected acoustic features and their differences in two planes. These results are indicative of a capability of the multi-modal imaging systems as described herein through bi-planar US imaging to monitor collagen fiber network (fibrosity of the tissue) degradation of cervical tissue during cervical remodeling by acquiring bi-planar images of orthogonal fiber planes. An anisotropic score (E) that represents the acoustic differences between the images acquired in sagittal (parallel to the fibers) and transverse (across the fibers) planes of the cervical tissue may be set forth below as Equation 1B:

$$E=\alpha_1\Delta BSP+\alpha_2\Delta BSC+\alpha_3\Delta AA+\alpha_4\Delta EAC+\alpha_5\Delta ESD+\alpha_6\Delta MGL+\alpha_7\Delta GLHW \quad \text{(Equation 1B)}$$

With respect to Equation 1B above, $\alpha_1$ to $\alpha_7$ are representative of coefficients to be optimized to achieve the most distinction between collagenous and degraded states.

Figures 12A, 12B:
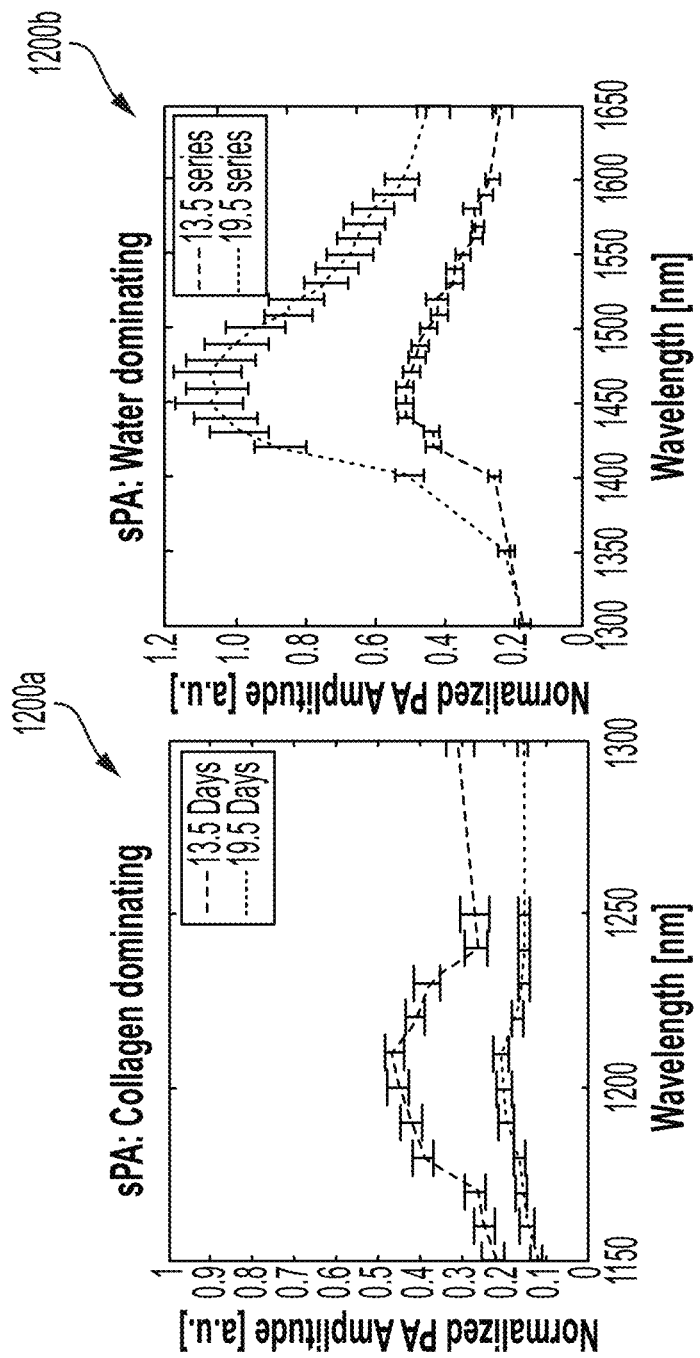
FIGS. 12A-12H illustrate example data indicative of collagen and water comparison levels in a plurality of murine cervix samples at different gestational ages, according to one or more embodiments shown and described herein.
Figure 12C:
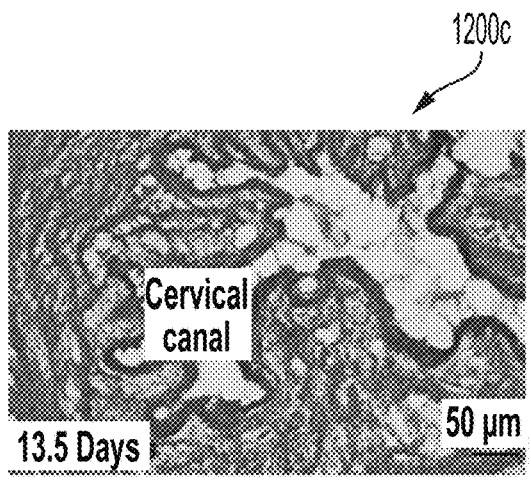
Figure 12D:
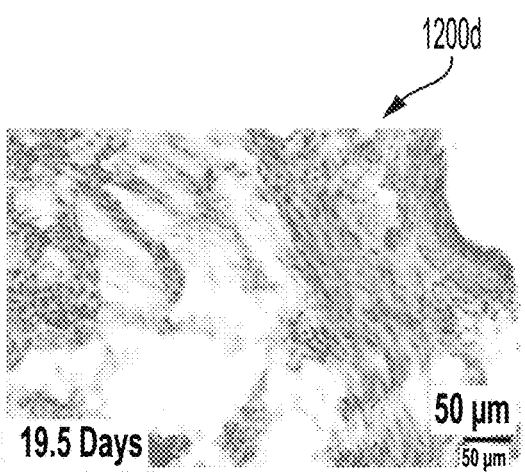

Referring to FIGS. 12A-12H, example data 1200a-1200h indicative of collagen and water comparison levels in a plurality of murine cervix samples at different gestational ages from an experiment are illustrated. The data is representative of collagen and water imaging results utilizing the imaging systems and devices as described herein. Murine cervix samples at different gestational ages were imaged within one hour after extraction. During the imaging procedure and transportation, the murine cervix samples were kept inside a storage solution as commercially available as and by Ambion® RNALater™. Wide-spectrum range spectroscopic photoacoustic (sPA) imaging from imaging in a range of from about 1150 nm to about 1650 nm was performed, and the laser energies at different wavelengths were recorded to normalize the acquired PA signals with respect to energy variations. In addition, the storage solution was spectroscopically imaged in the same wavelength range to assure no interference from the background solution. Upon finishing the studies, the tissue was washed with PBS, embedded into optimal cutting temperature (OCT) compound, and underwent snap-freezing using liquid nitrogen, followed by storage at −80° C. prior to section and histologic analyses. FIGS. 12A-12H summarize the sPA results of two groups of six murine cervices at 13.5 (mid pregnancy) and 19.5 (ripened cervix at labor) days post coitum (dpc). The sPA signal is divided into two separate bandwidths: 1100-1300 nm where collagen absorption peaks at around 1200 nm and water absorption is flat. Since the lipid content of cervical tissue is not significant, its absorption can be disregarded in sPA calculations. The second sPA band is 1300-1650 nm where the water is the dominant absorber. FIGS. 12A-12B illustrate that the degradation of signal arises from collagen at 19.5 dpc compared to 13.5 dpc, indicative of a reduced signal from the collagen network with a ripened cervix. By contrast, the signal from the water is significantly increased in the ripened cervix (19.5 dpc). With respect to a histological analysis, through use of a cryostat, 10-μm sections of the frozen tissues were stained using a stain kit such as the Picrosirius Red Stain Kit as commercially available from Polysciences, Inc. and imaged under a light microscope to examine the stained collagen. To semi-quantitatively determine the amount of collagen and non-collagen proteins in each tissue, a Sirius Red/Fast Green collagen staining was used. Hematoxylin and Eosin (H&E) staining of the murine cervices at 13.5 dpc and 19.5 dpc are shown in FIGS. 12C-12D.

Figure 12E:
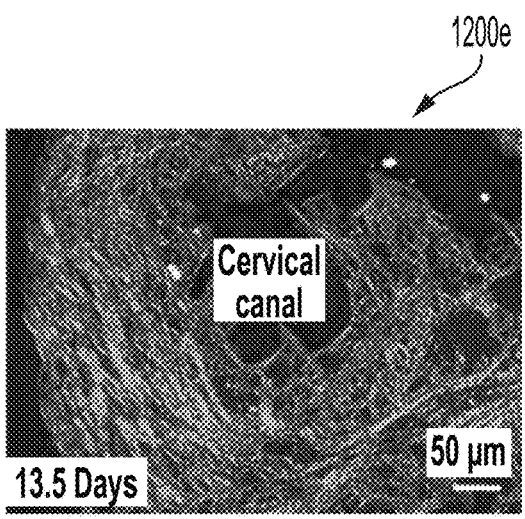
Figure 12F:
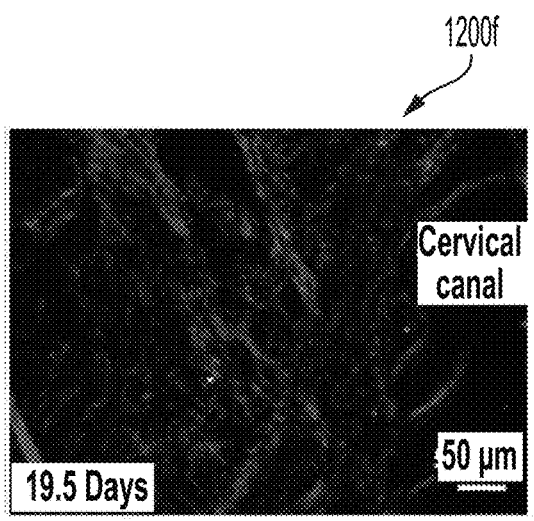
Figure 12G:
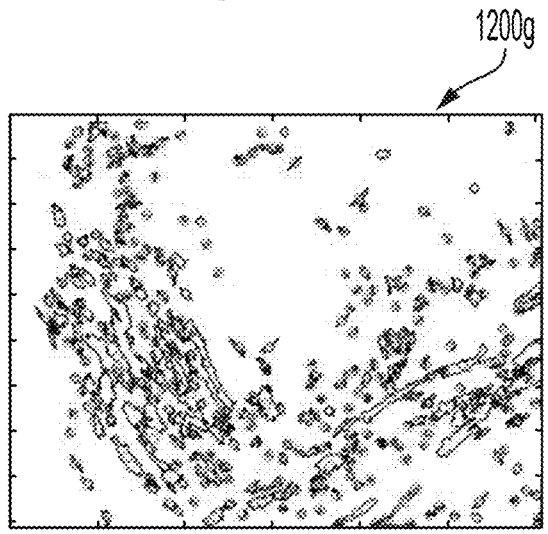
Figure 12H:
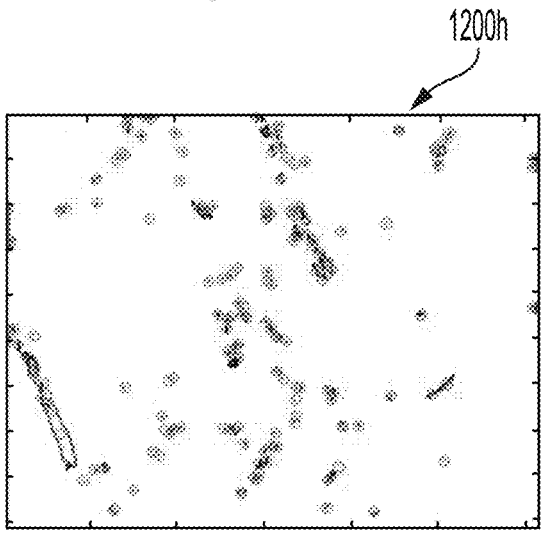

The results depict the presence of edema (i.e., increased water content) in the ripened mice cervices at 19.5 dpc. Thus, at 19.5 dpc, general organization of tissue is lost, and endocervical mucosa is not present. Further, fibrous components disappear, and the presence of an amorphous material is appreciated between muscular cells. A transversal slide of the murine uterine cervices at 13.5 dpc, stained with Sirius Red and microscopically imaged under polarized light, is shown in FIG. 12E. A dense, organized concentric network of collagen fibers has birefringence and appears as red/yellow rod-like structures. By contrast, at 19.5 dpc (ripened cervix), the degradation of the collagen network led to no clear appearance of collagen fibers, and the tissue had significantly lower collagen fiber content (FIG. 12F). Further, mean $CW_R$ values of 13.5 and 19.5 dpc were measured as 60.45 and 41.04, respectively. The Sirius Red-stained images were further processed using pattern analysis and image quantification algorithms to extract radiomic features, such as intensity measurement, the size of collagen regions, and collagen fiber orientations (FIGS. 12G-12H).

Figure 13B:
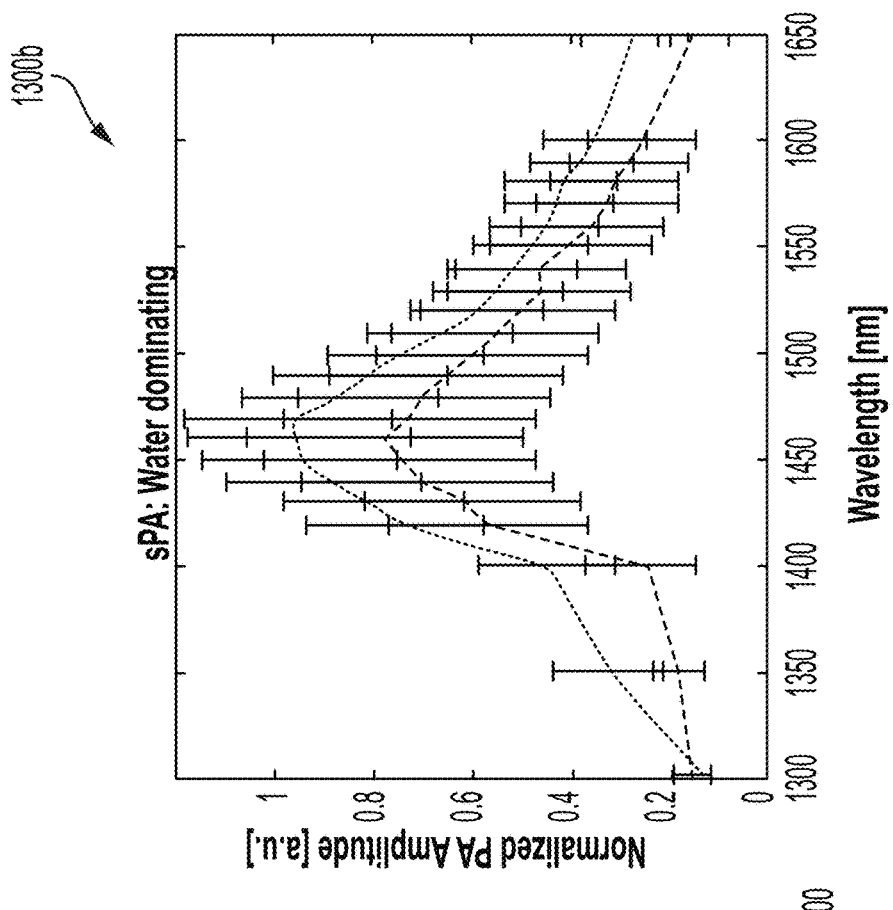
FIGS. 13A-13F illustrate example data indicative of collagen and water comparison levels in a plurality of human cervix samples of pregnant women at C-section and non-pregnant women, according to one or more embodiments shown and described herein.
Figure 13A:
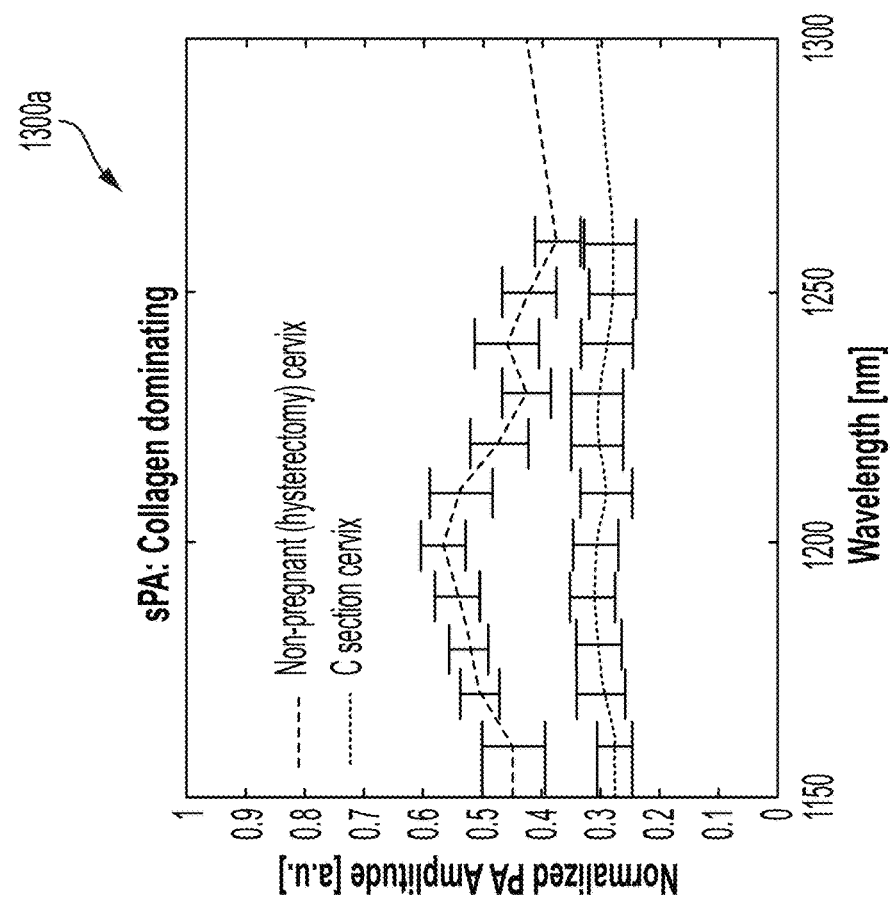
Figure 13C:
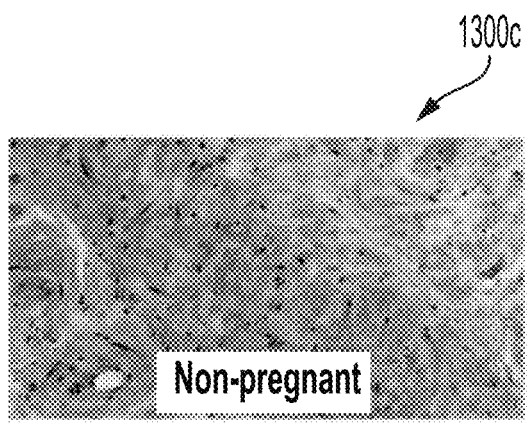
Figure 13D:
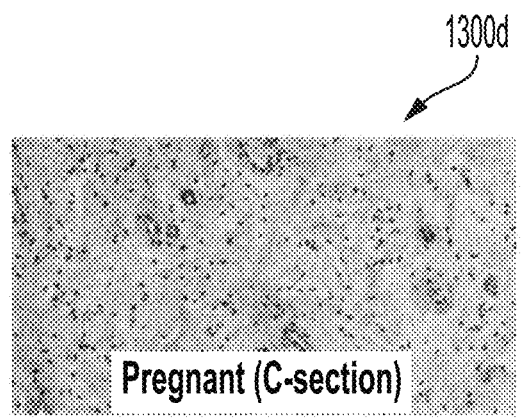
Figure 13E:
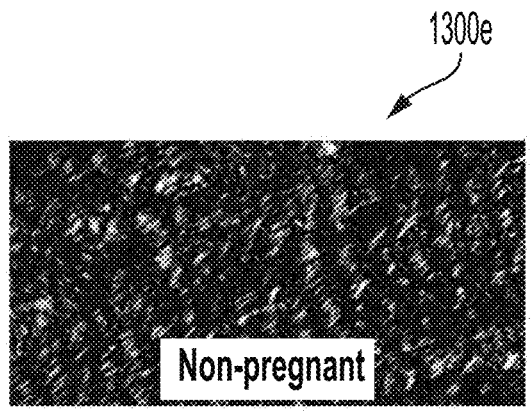
Figure 13F:
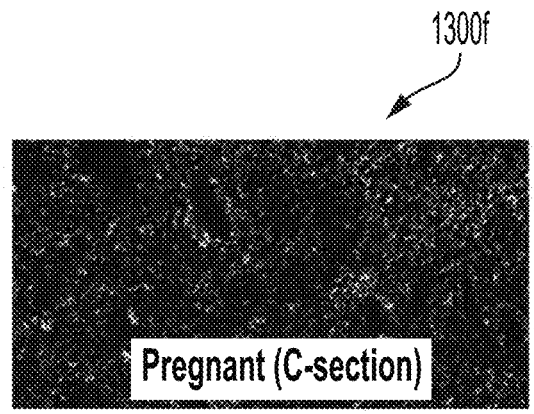
Figure 14:
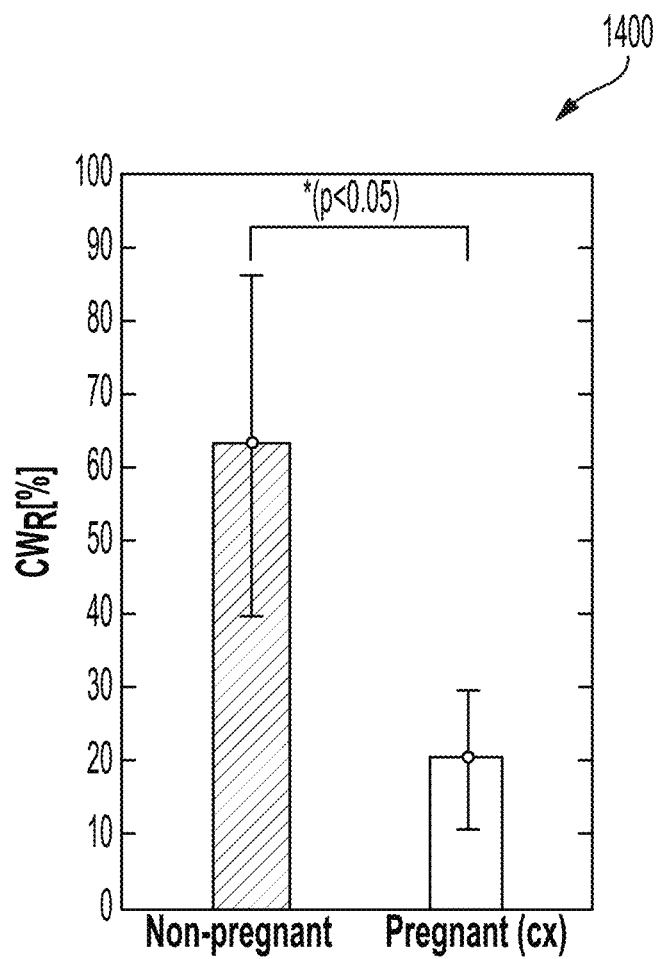
FIG. 14 illustrates a graphical comparison indicative of a collagen to water ratio in non-pregnant women compared to pregnant women, according to one or more embodiments shown and described herein.

Referring to FIGS. 13A-14, FIGS. 13A-13F illustrate example data 1300a-1300f indicative of collagen and water comparison levels in a plurality of human cervix samples of pregnant women at C-section and non-pregnant women, and FIG. 14 illustrates a graphical comparison indicative of a collagen to water ratio in non-pregnant women compared to pregnant women. The legend of FIG. 13A also applies to FIG. 13B. In particular, an experiment was conduct in which cervical biopsy samples obtained after hysterectomies and after cesarean sections (C-sections) were examined. Group 1 including 10 pre-menopausal women (non-pregnant cervix), and Group 2 included 10 women with normal pregnancies at term undergoing an elective C-section (pregnant cervix). Given that the sizes of the excised tissue samples were small for US microstructure and VE imaging, only sPA imaging was performed. A sample collection included biopsies measuring 5 mm³ that were collected at the time of hysterectomy or cervical biopsy. The biopsies were collected at 12 o'clock of the ectocervix and were immediately placed in storage solution as described herein. The samples underwent sPA measurement and were then placed in formaldehyde for histopathologic evaluation. All human tissue experiments were performed under signed informed consent.

FIGS. 13A-13F show sPA imaging results of the sampled non-pregnant and pregnant cervices. Similar to the murine experiment of FIGS. 12A-12H, sPA signals were shown in separate bandwidths of 1100-1300 nm and 1300-1650 nm. In FIG. 13A, a clear decrement of signal arising from collagen (at 1150 nm to 1250 nm) was observed for pregnant cervical tissue excised from C-section patients who underwent cervical biopsy. In addition, the water content of the pregnant cervical tissue was significantly increased in FIG. 13B according to sPA imaging results. Microscopic images of tissue taken from non-pregnant human cervices are illustrated to show compact collagen bundles with minimal or no intervening edema (FIG. 13C). When examined using a stain such as the Sirius Red stain, the collagen fibers show formation of bundles with distinct fasciculation (FIG. 13E). By contrast, the pregnant human cervix shows loose collagen fibers with no discrete bundles and with edema separating the collagen fibers (FIG. 13D). The absence of discrete collagen bundles, as well as the loss of the distinct fasciculation seen in the non-pregnant human cervix, is evident (FIG. 13F). FIG. 14 further illustrates a graphical comparison indicative of a collagen to water ratio in non-pregnant women compared to pregnant women of this experiment, showing that non-pregnant women have a higher collagen to water ratio than the pregnant women of the sample.

Use of the probe device with a system to provide such US, VE, and PA imaging allows for a multi-parametric, multi-modal, non-invasive, and real-time assessment of risk of preterm delivery of an expectant mother through imaging of a cervix through a vaginal canal of the expectant mother. Doppler US and US flow information may be obtained through tuning of pulse-echo parameters in a US scanner. PA signals representative of acoustical signals generated by tissue in response to ultrashort laser pulses in, for example, a nanosecond range, may convey information about optical absorption properties of the tissue. While PA signals may be acquired and treated similarly to US echo signals, they are able to provide different information with respect to tissue absorption characteristics such a differential between oxy-hemoglobin and deoxy-hemoglobin in the blood vessels associated with the tissue. For example, difference between the optical absorption spectrums of oxy-hemoglobin and deoxy-hemoglobin enable spectroscope PA technology, which represents a PA signal as two or more wavelengths, to measure respective concentrations of oxy-hemoglobin and deoxy-hemoglobin and thus provide a blood oxygen saturation ($SO_2$). Light wavelengths to measure $SO_2$ may be below 900 nm, for example, and thus a mobile and compact laser(s) with an embedded cooling system may be utilized with the probe device.

Figure 18:
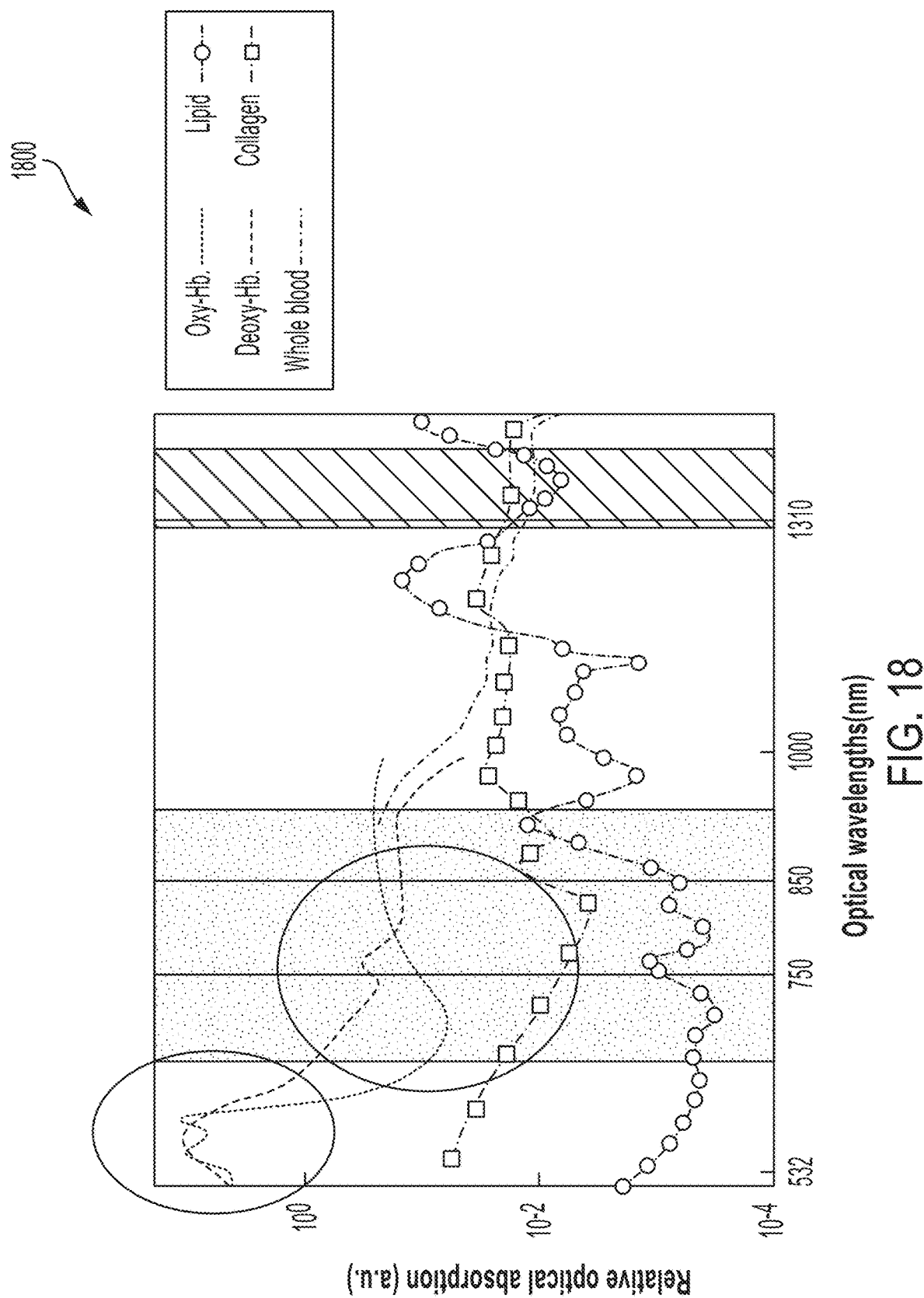
FIG. 18 illustrates graphical results indicative of PA imaging utilizing an endogenous contrast in which a PA signal is generated proportional to optical absorption of laser pulses in tissue at different wavelengths to track and compare variety of absorption metrics for different biomarkers at the different wavelengths and illustrating an optional wavelength range for oxygen saturation measurements, according to one or more embodiments shown and described herein.
Figure 19:
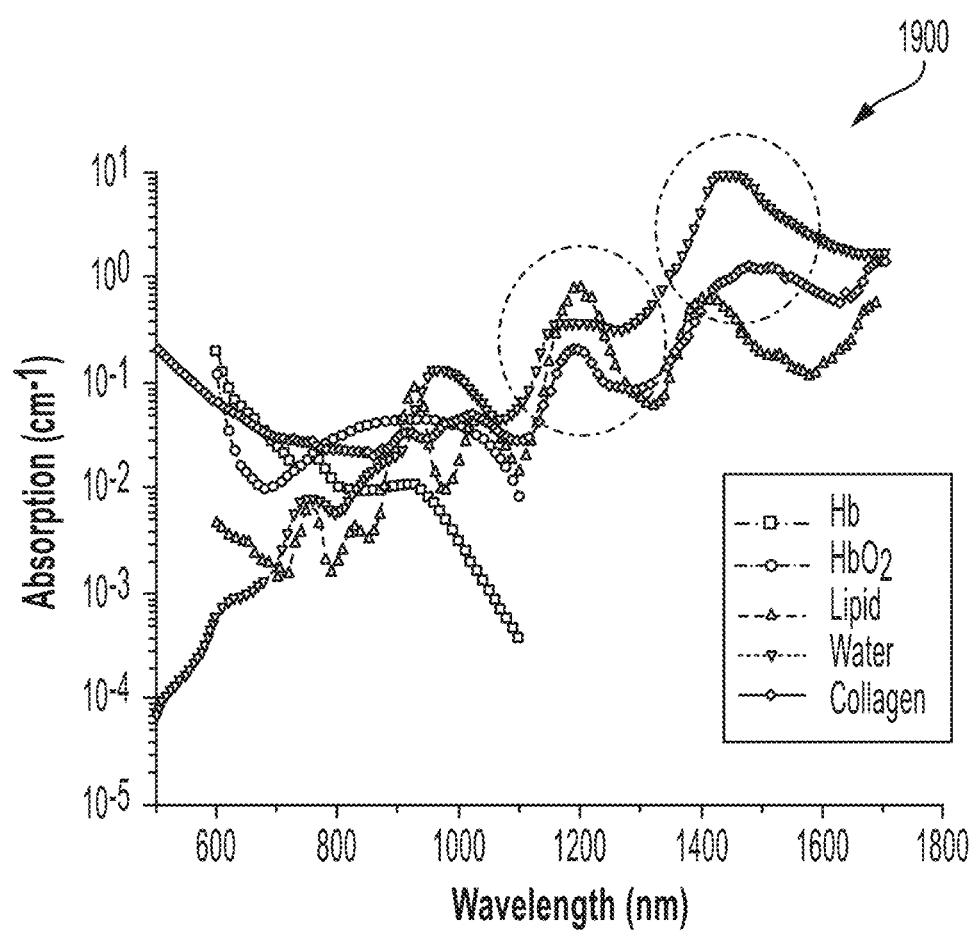
FIG. 19 illustrates graphical results indicative of PA imaging utilizing an endogenous contrast in which a PA signal is generated proportional to optical absorption of laser pulses in tissue at different wavelengths to track and compare variety of absorption metrics for different biomarkers at the different wavelengths and illustrating optional wavelength ranges for collagen/water ratio measurements, according to one or more embodiments shown and described herein.

FIG. 18, for example, illustrates a chart 1800 depicting a difference in relative optical absorption in cervical tissue of a PA signal at a variety of wavelengths with respect to parameters such as oxy-hemoglobin (HbO), deoxy-hemoglobin (Hb), whole blood (such as total hemoglobin), lipid, and collagen. Additional detail regarding the system including, but not limited to, an associated architecture of the system and a comparison between oxygen saturation measurements through PA and gold-standard blood gas analyzer is provided in FIG. 15.

The acoustic signals from respective US echoes and PA laser pulses may be acquired by a US machine that is communicatively coupled to the probe device 100 in an imaging system, and the probe device may be enabled to control a transmit/receiving timing of the signals to synchronize the US machine with the PA laser pulses to acquire interleaved US and PA images on a graphical user interface of the US machine. For example, an imaging sequence may be on the US machine to acquire and provide real-time US and PA frames for simultaneous display on the graphical user interface of the US machine. The interleaved image may be displayed as an image of the cervix including an image of blood vessels.

Oxygen saturation values may be extracted through a spectroscopic PA (sPA) method in which an amplitude of a PA signal is proportional to an optical absorption of absorbers including oxy-hemoglobin and deoxy-hemoglobin. In embodiments, the PA signals are filtered such as through being passed through a Hamming window bandpass filter to localize the signal in a sample holder and minimize spectral leakage. For each signal, a signal amplitude may be computed by integrating an envelope of each signal using, for example, a Hilbert transform. An average and standard deviation of the signal amplitude may further be computed.

Figure 15:
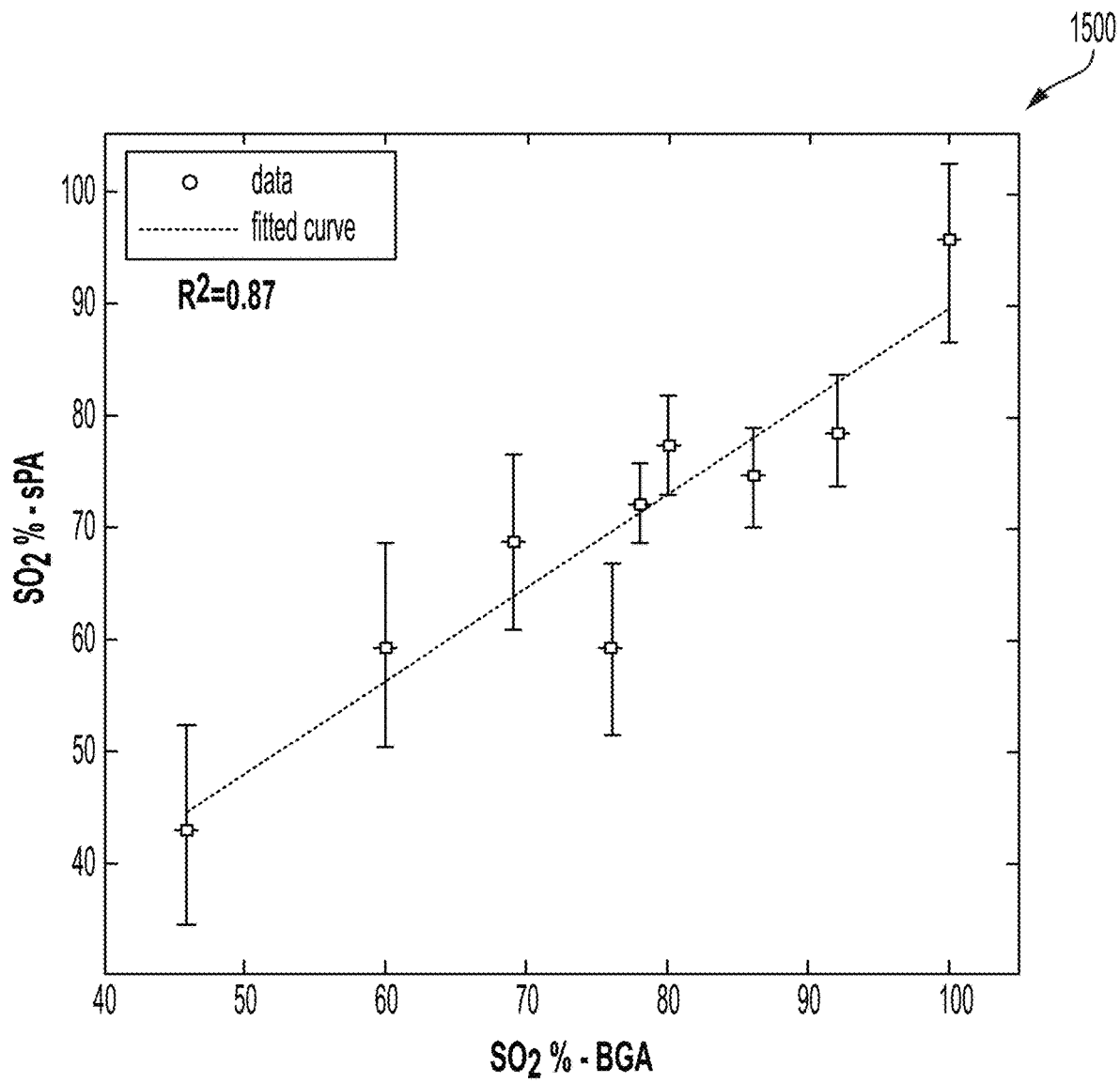
FIG. 15 illustrates a graphical representation of data indicative of a close correlation between oxygen saturation ($SO_2$) measured by the probe of FIGS. 1A-1C versus measured by a blood gas analyzer at a plurality of wavelengths, according to one or more embodiments shown and described herein.

Referring to a model 1500 of FIG. 15, principles of sPA imaging and spectral unmixing may be used to measure $SO_2$ with known molar extinction coefficients of Hb and $HbO_2$. To evaluate an accuracy of the developed sPA algorithm as described herein to measure $SO_2$, a set of experiments was performed in which the blood $SO_2$ was altered in fresh, heparinized sheep blood, using $O_2$ and $N_2$ gas purges within a sealed, closed loop circulation system. Briefly, a gasexchange chamber was built and connected to a sealed, closed loop tubing that was partially placed in a water tank for US/PA imaging. After several trials and calibrations, the gas flows were adjusted to change the blood oxygenation from a fully oxygenated state at approximately 100% to $SO_2$ of approximately 46%. Further, sPA imaging was performed at $\lambda$=752 nm, 780 nm, and 800 nm, and blood $SO_2$ measured by PA imaging was compared to a gold-standard blood gas analyzer, such as one commercially available as OPTI® CCA, by OPTI Medical Systems, Inc., as well as to an optical oxygen-sensing probe, such as one commercially available by neoFox Ocean Optics Inc. FIG. 15 illustrates the PA $SO_2$ measurements versus the gold-standard blood gas analyzer (BGA), which resulted in a high correlation ($R^2$=0.87) that was found between sPA measurements of blood $SO_2$ and the BGA, indicative of a reliability of sPA with multi-modal probes and system as described herein to measure blood $SO_2$.

Figure 16B:
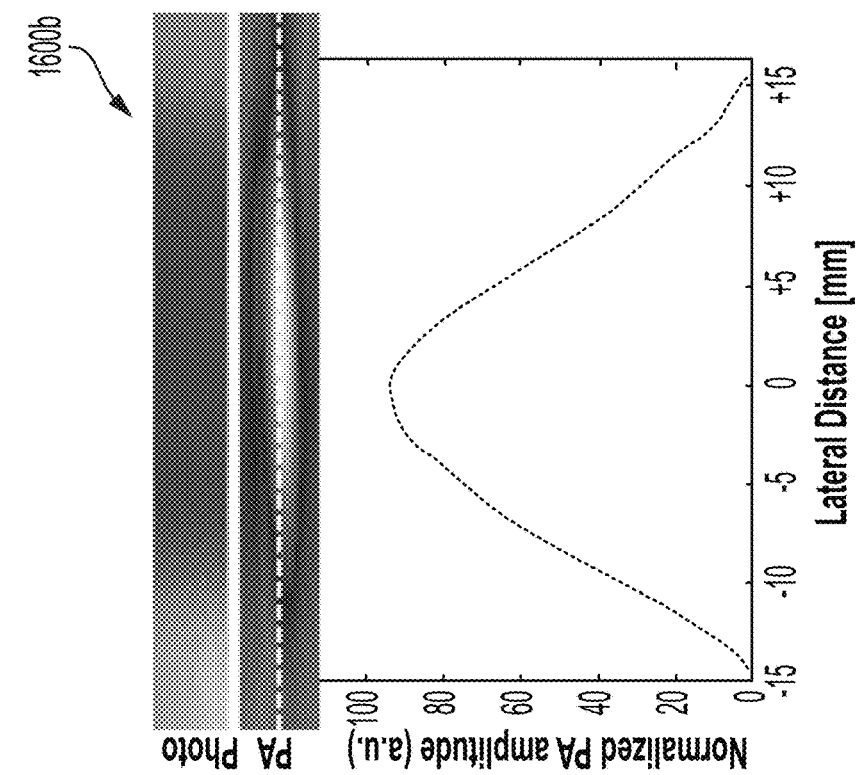
FIGS. 16A-16B respectively illustrate graphical results indicative of PA imaging of total hemoglobin in tissue utilizing the probe of FIGS. 1A-1C with respect to sensitivity in FIG. 16A and spatial matching in FIG. 16B, according to one or more embodiments shown and described herein.
Figure 16A:
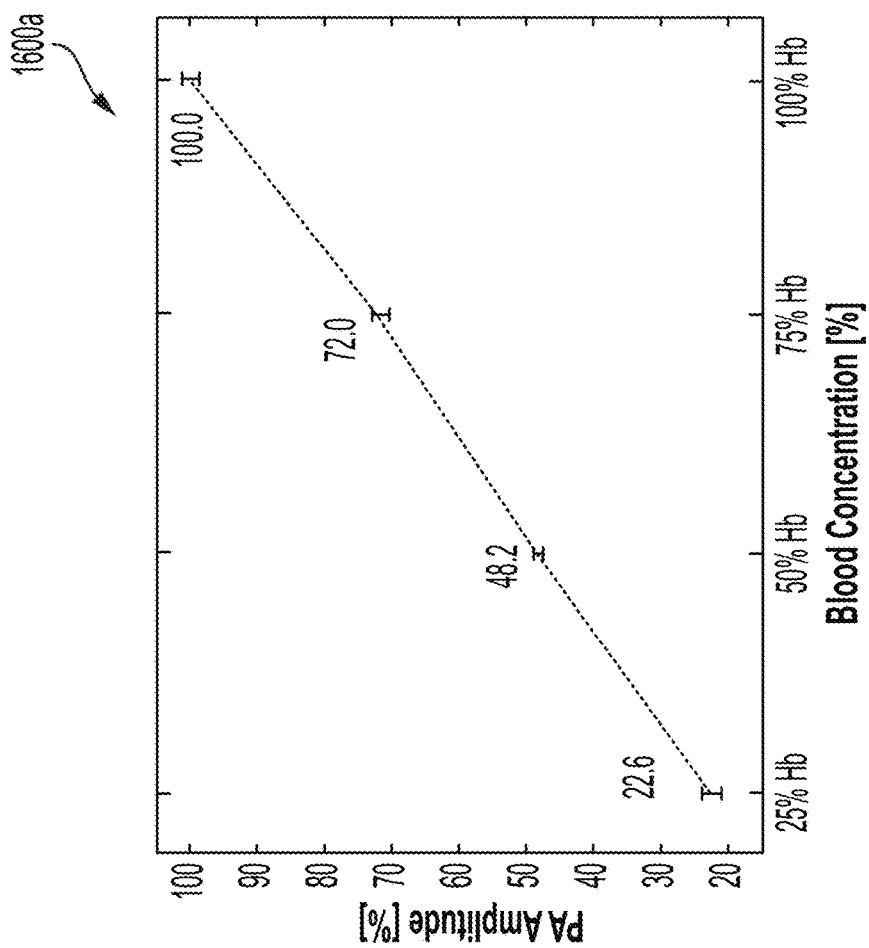

Referring to charts 1600a-1600b of respectively FIGS. 16A-16B, the multi-modal systems as describe herein may be utilized to measure cervical tissue vascularity or total Hb content. Tissue blood content as an indicator for tissue vascular density may be determined by imaging a total Hb present in the tissue. PA imaging has been shown to be an effective tool in measuring hemoglobin concentration in the tissue by imaging the peak absorption of red blood cells ($\lambda$=532 nm). To test PA imaging sensitivity to total blood hemoglobin with respect to the multi-modal imaging system as described herein, adult human blood was used to make hemoglobin samples at different dilution ratios. PA imaging of the samples (FIG. 16A, which shows a normalized PA signal at different dilution levels) graphically represents an indication of the proportionality of PA amplitude and concentration of Hb. In another set of experiments, a tissue-mimicking phantom was made from porcine gelatin, and human blood was placed in a hole embedded inside the phantom. After 48 hours, the blood perfused to the surrounding background tissue-phantom. The phantom was imaged at $\lambda$=532 nm, and both PA image and lateral profile of signals in FIG. 16B (i.e., the PA signal of diffused blood into a tissue-mimicking background) clearly show the ability of PA imaging to track the variation in a blood concentration.

Figure 17B:
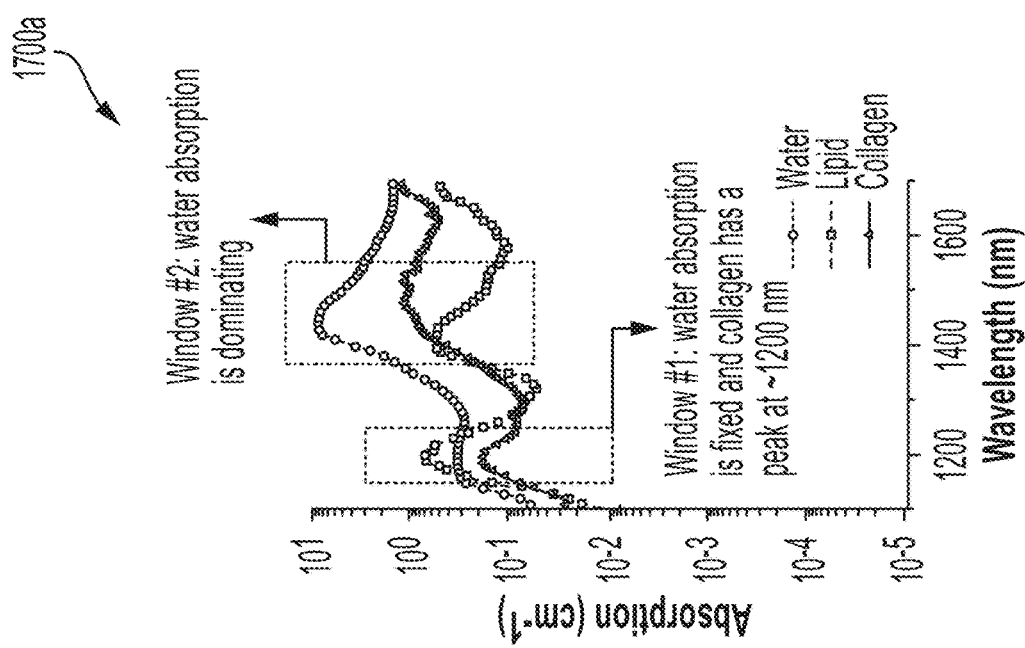
FIGS. 17A-17B respectively illustrate graphical results indicative of PA imaging of collagen and water with respect to collagen gel phantoms, showing PA imaging windows at different wavelengths in FIG. 17A and a close correlation of PA amplitude and collagen measurement data in FIG. 17B, according to one or more embodiments shown and described herein.
Figure 17A:
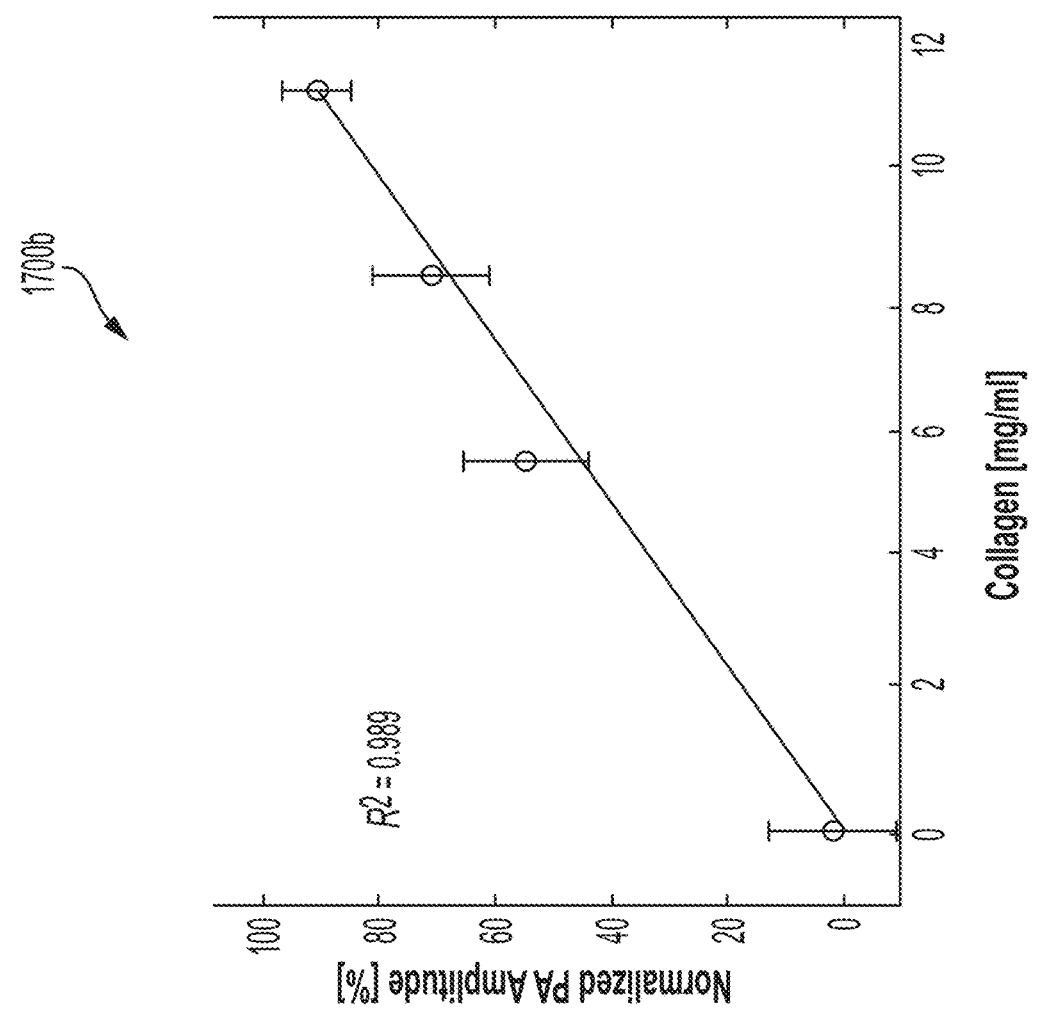

Referring to charts 1700a-1700b of respectively FIGS. 17A-17B, results of an experimentation described below are shown illustrating an optical absorption of collagen and water (FIG. 17A) and sPA measurement of a collagen to water ratio in phantoms including different concentrations of collagen and a blank sample such as distilled water (FIG. 17B). FIGS. 17A-17B illustrate the use of sPA to determine the collagen (C) and water (W) content (C/W ratio) of tissue-mimicking phantoms and excised tissue samples in the experimentation. The sPA C/W ratio ($CW_R$) measurement algorithm included two steps. A first step included an amplification of the PA signal acquired in the range of 1150 to 1250 nm, at which collagen has a peak absorption, to detect relative small variations. Within $\lambda$=1150 to 1250 nm, water absorption remains constant, but collagen absorption has a clear peak. Although the collagen has an absorption peak among these wavelengths, an absolute value is still relatively weak compared to the water absorption (FIG. 17A). Therefore, a signal amplification algorithm was utilized to amplify the PA signal derived from collagen as Equation 3 set forth further below, where $\lambda$ will be 1150, 1200, or 1250 nm. This amplification assisted to amplify the signal coming from the collagen since water has constant absorption in the range of 1150 to 1250 nm. A second step included calculating the $CW_R$ using the amplified PA signal. Assuming a uniform fluence of the light inside the tissue, Equation 4 set forth further below was utilized, where PA($\lambda$) is the amplitude of PA signal; $\epsilon$ represents extinction coefficients; and $\Delta\epsilon(\lambda_n)=\epsilon(C, \lambda_n)-\epsilon(W, \lambda_n)$ is the extinction coefficients difference at each wavelength. Further, $\lambda_1$ and $\lambda_2$ are to be chosen from respective pairs of (1150 and 1200 nm) and (1200 and 1250 nm), and the measured values are averaged to achieve $CW_R$. This spectroscopic process was performed for each pixel of the image guided by a B-mode US to identify the true location of the cervical tissue. Further, water has a strong absorption peak at $\lambda$ of approximately 1450 nm. The $CW_R$ calculation method was further able to be enhanced by including sPA data acquired between 1400 and 1600 nm. To demonstrate the utility of sPA in measuring $CW_R$, collagen blocks were made of different concentrations of Type I Collagen from murine samples such as a rat tail as commercially available from Corning® Inc. with a concentration of 11.2 mg/ml. To form the different concentrations of collagen gels, liquid collagen was mixed into 1× phosphate buffered saline (PBS) and then fixed to the gel by adding NaOH and 7.5% sodium bicarbonate, followed by incubation at 37° C. Following, sPA imaging was performed, and the results of collagen content in the phantoms are shown in FIG. 17B. A blank sample of distilled water was also imaged to validate the sensitivity of the multi-modal, spectroscopic method as described herein in detecting $CW_R$.

As a non-limiting example, the PA signals may be analyzed to determine correlation maps and a blood oxygen saturation map. Both maps are based on extinction coefficients. The correlation maps include an oxygenation correlation map (OCM) and a deoxygenation correlation map (DOCM). The OCM may be determined based on a correlation between a known absorption of oxy-hemoglobin (HbO) and a recorded PA signal, and the DOCM may be determined based on a correlation between a known absorption of deoxy-hemoglobin (Hb) and the recorded PA signal. The result may be normalized, and a 256 levels color map may be applied on the normalized result. Determination of the correlation maps assists with determining the extinction coefficients. Equation 2 below sets for an equation to calculate oxygen saturation in blood:

$$SO_2 = \frac{[HbO]}{[HbO]+[Hb]} = \frac{PA(\lambda_2)*\varepsilon(Hb,\lambda_1)-PA(\lambda_1)*\varepsilon(Hb,\lambda_2)}{PA(\lambda_1)*\Delta\varepsilon(\lambda_2)-PA(\lambda_2)*\Delta\varepsilon(\lambda_2)} \quad \text{(Equation 2)}$$

In Equation 2 above, $\Delta\epsilon(\lambda_n)=\epsilon(HbO, \lambda_n)-\epsilon(HbO, \lambda_n)$ for each wavelength n and is representative of a difference in the extinction coefficient for each wavelength. The oxygen saturation ($SO_2$) may be calculated for all measured PA signals to generate a percentage value, and more than two wavelengths may be measured. A final oxygen saturation result may be an average of all pairs of PA signals.

Other parameters, including an amplified PA signal value as shown in Equation 3 below and a collagen (C) to water (W) ratio calculation ($CW_R$) of cervical tissue as shown in Equation 4 below utilizing values from two different wavelengths, may be estimated at least partially based on the obtained measurements of oxygen saturation of the cervix.

$$Amplified_{PA} = \frac{(PA_\lambda)^2}{(PA_{@1250nm})} * \frac{(PA_{@1200nm})}{(PA_{@1150nm})} \quad \text{(Equation 3)}$$

-continued $$CW_R = \frac{[\text{Collagen}]}{[\text{Water}] + [\text{Collagen}]} = \qquad \text{(Equation 4)}$$
$$\frac{PA(\lambda_2) * \varepsilon(C, \lambda_1) - PA(\lambda_1) * \varepsilon(C, \lambda_2)}{PA(\lambda_1) * \Delta\varepsilon(\lambda_2) - PA(\lambda_2) * \Delta\varepsilon(\lambda_2)}$$

In Equation 4 above, $\Delta\varepsilon(\lambda_n)=\varepsilon(C, \lambda_n)-\varepsilon(W, \lambda_n)$ for each wavelength n and is representative of a difference in the extinction coefficient for each wavelength. In embodiments, the probe device may be used alongside the transabdominal US (and PA) to determine oxygen measurements as described herein.

In an embodiment, and referring to FIGS. 1D-3, an imaging system, such as the imaging system 100 as described herein, may be used for implementing computer and software-based methods to provide a real-time assessment of a metabolic rate of oxygen in a cervix of an expectant mother as well as to provide cervical tissue characteristics through use of multi-modal imaging such as combined US, VE, and PA imaging techniques described herein to predict risk of preterm birth. The imaging system may utilize sPA imaging with tunable short laser pulses to excite the tissue and probe optical properties (absorption and scattering) of the cervical tissue via acquiring generated acoustic waves, which is the result of laser-tissue interaction and subsequent thermoelastic expansion. The multi-modal imaging system described herein acquires pulse-echo US radiofrequency (RF) data followed by PA signal acquisition at multiples wavelengths ($\lambda$): $\lambda=532$ nm for total hemoglobin (Hb), $\lambda=752$, 780, and 800 nm for tissue oxygenation measurement, and A between 1150 and 1600 nm for the measuring collagen-to-water ratio, with such optional and desirable ranges as illustrated in FIGS. 17A-19 through respective charts 1700a-1900.

The imaging system may be implemented along with using a graphical user interface (GUI) displaying a home screen for a user to access the platform and/or view a dashboard as described herein and that is accessible at a user workstation (e.g., a mobile and/or stationary computing device such as a computer that may be an US machine, for example). The system includes a communication path, one or more processors, a memory component, transducer probe device as described herein, a storage or database, an imaging module, a network interface hardware, a network, a server, and at least one computer. The various components of the system and the interaction thereof will be described in detail below.

While only one application server and one user workstation computer is illustrated, the system can include multiple workstations and application servers containing one or more applications that can be located at geographically diverse locations across a plurality of physical sites. In some embodiments, the system is implemented using a wide area network (WAN) or network, such as an intranet or the Internet, or other wired or wireless communication network that may include a cloud computing-based network configuration. The workstation computer may include digital systems and other devices permitting connection to and navigation of the network. Other system variations allowing for communication between various geographically diverse components are possible. The lines depicted in the system images indicate communication rather than physical connections between the various components.

As noted above, the system includes the communication path. The communication path may be formed from any medium that is capable of transmitting a signal such as, for example, conductive wires, conductive traces, optical waveguides, or the like, or from a combination of mediums capable of transmitting signals. The communication path communicatively couples the various components of the system. As used herein, the term "communicatively coupled" means that coupled components are capable of exchanging data signals with one another such as, for example, electrical signals via conductive medium, electromagnetic signals via air, optical signals via optical waveguides, and the like.

As noted above, the system includes the processor that can be any device capable of executing machine readable instructions. Accordingly, the processor may be a controller, an integrated circuit, a microchip, a computer, or any other computing device (i.e., such as a graphics processing unit (GPU)). The processor is communicatively coupled to the other components of the system by the communication path. Accordingly, the communication path may communicatively couple any number of processors with one another, and allow the modules coupled to the communication path to operate in a distributed computing environment. Specifically, each of the modules can operate as a node that may send and/or receive data.

As noted above, the system includes the memory component which is coupled to the communication path and communicatively coupled to the processor. The memory component may be a non-transitory computer readable medium or non-transitory computer readable memory and may be configured as a nonvolatile computer readable medium. The memory component may comprise RAM, ROM, flash memories, hard drives, or any device capable of storing machine readable instructions such that the machine readable instructions can be accessed and executed by the processor. The machine readable instructions may comprise logic or algorithm(s) written in any programming language such as, for example, machine language that may be directly executed by the processor, or assembly language, object-oriented programming (OOP), scripting languages, microcode, etc., that may be compiled or assembled into machine readable instructions and stored on the memory component. Alternatively, the machine readable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components. In embodiments, the system may include the processor communicatively coupled to the memory component that stores instructions that, when executed by the processor, cause the processor to perform one or more tool functions as described herein.

As noted above, the system comprises the display such as a GUI on a screen of the computer for providing visual output such as, for example, US, VE, and/or PA imaging and/or associated physiological measurement information based on received US, VE, and/or PA signals. The computer may include one or more computing devices across platforms, or may be communicatively coupled to devices across platforms, such as mobile smart devices including smartphones, tablets, laptops, and/or the like.

The GUI may present a user with a home screen, for example, as described herein, which home screen may display one or more views as images provided through the imaging module, as described in greater detail above with respect to imaging techniques based on US, VE, and/or PA signals obtained from the transducer probe device as described herein. The display on the screen of the computer is coupled to the communication path and communicatively coupled to the processor. Accordingly, the communication path communicatively couples the display to other modules of the system. The display can include any medium capable of transmitting an optical output such as, for example, a cathode ray tube, light emitting diodes, a liquid crystal display, a plasma display, or the like. Additionally, it is noted that the display or the computer can include at least one of the processor and the memory component. While the system is illustrated as a single, integrated system, in other embodiments, the systems can be independent systems. As will be described in further detail below, the processor may process the input signals received from the system modules and/or extract information from such signals.

The system includes the network interface hardware for communicatively coupling the system with a computer network such as network. The network interface hardware is coupled to the communication path such that the communication path communicatively couples the network interface hardware to other modules of the system. The network interface hardware can be any device capable of transmitting and/or receiving data via a wireless network. Accordingly, the network interface hardware can include a communication transceiver for sending and/or receiving data according to any wireless communication standard. For example, the network interface hardware can include a chipset (e.g., antenna, processors, machine readable instructions, etc.) to communicate over wired and/or wireless computer networks such as, for example, wireless fidelity (Wi-Fi), WiMax, Bluetooth, IrDA, Wireless USB, Z-Wave, ZigBee, or the like.

Data from various applications running on computer can be provided from the computer to the system via the network interface hardware. The computer can be any device having hardware (e.g., chipsets, processors, memory, etc.) for communicatively coupling with the network interface hardware and a network. Specifically, the computer can include an input device having an antenna for communicating over one or more of the wireless computer networks described above.

The network can include any wired and/or wireless network such as, for example, wide area networks, metropolitan area networks, the Internet, an Intranet, satellite networks, or the like. Accordingly, the network can be utilized as a wireless access point by the computer to access one or more servers, which generally include processors, memory, and chipset for delivering resources via the network. Resources can include providing, for example, processing, storage, software, and information from a server to the system via the network. Additionally, it is noted that the one or more servers can share resources with one another over the network such as, for example, via the wired portion of the network, the wireless portion of the network, or combinations thereof.

The imaging system may include an acquisition system communicatively coupled to the transducer probe device through one or more components and wires of the communication path. The acquisition system may be communicatively coupled to the computer through either a wired or wireless connection. The acquisition system may be a US real-time data acquisition system including 128 channels.

Further, the one or more processors of the system includes a FPGA based control unit communicatively coupled to a laser and the acquisition system. The FPGA may be high speed at about 100 MHz or faster and may be center timing unit in the system. The laser is communicatively coupled to an optical parametric oscillator (OPO) that converts an input laser wave with a frequency into two output waves of lower frequency. A laser assembly including the laser and OPO may operate at 30 Hz and utilize real-time pulse energy monitoring. The transducer probe device in FIG. 2 is illustrated as sending signals to (such as tunable laser pulses) and receiving signals from an object schematically disposed below the transducer probe device. In embodiments, the system may have two or more lasers (that each may or may not be tunable) that drive all or a sub group of fibers in order to achieve faster spectroscopic PA imaging. The transducer probe device in FIG. 3 is illustrated as sending sound waves (i.e., US waves) and received reflected US waves back through a transducer of the probe device.

With respect to the PA imaging mode of the imaging system of FIG. 2, cervical tissue may be irradiated with a short laser pulse of, for example, 5-7 ns. Optical energy is absorbed by the cervical tissue. Such optical absorption leads to a rapid thermal expansion of the cervical tissue. Further, with respect to the US imaging mode of the imaging system of FIG. 3, as cervical tissue is irradiated with the short laser pulse, acoustic transients may be generated from the pulses, and, along with reflected US waves, may be recorded using the US transducer and then submitted through one or more signals to generate an image on the US machine display. With respect to PA imaging, tissue is thus irradiated with a short laser pulse, optical energy is absorbed by the tissue and converted to thermal energy, optical absorption of short pulses of light leads to a rapid thermal expansion of tissue and generation of acoustic (pressure) transients, and an acoustic signals is recorded using the US transducer of a multi-modal probe device as described herein to form a multi-modal image. Such acoustic (PA) signals arise from small molecules of the cervical tissue, providing both endogenous (molecular composition/functional tissue information) and exogenous (molecular imaging) information.

The probe device with use of one or more systems as described herein provides for a direct, accurate, and real-time monitoring blood oxygen saturation in the cervix of an expectant mother as well as other cervical tissue characteristics as described herein to detect a risk of preterm birth through use of US, VE, and PA imaging.

Analysis of tri-modal US, VE, and PA biomarkers of cervical tissue of an expectant mother by multi-modal imaging devices and systems as described herein may be divided per modality. By way of an example, and not as a limitation, for a modality of a bi-planar US microstructural imaging as described herein, a biomarker analysis may identify (a) acoustic parameters and (b) tissue anisotropic features. The acoustic parameters may include acoustic attenuation, backscattering coefficient, backscattering power, effective acoustic concentration, and US scatterer density and scatterer size (i.e., diameter). The tissue anisotropic features may include features obtained from US image features such as apparent echogenicity along and across collagen fibers. A biological relevance to cervical ripening/modeling of use of bi-planar US imaging may include a disorganization of a collagen network during remodeling that changes the acoustic attenuation, scattering density, and backscattering coefficient/power. As cervical tissue remodeling progresses, prostaglandin production increases and collagen fibers become thicker. However, collagen fiber degradation in cervical tissue reduces anisotropic characteristics of the cervical tissue and is detectable by US imaging in two orthogonal (sagittal and transverse) planes (parallel to and across collagen fibers) as described herein.

Further, for a modality of a sPA imaging as described herein, a biomarker analysis may identify (a) collagen remodeling (i.e., collagen network disorganization), (b) tissue hydration (i.e., water content of the cervical tissue and a collagen to water ratio in the cervix), (c) blood perfusion/tissue vascularity/tissue hemoglobin content; and/or (d) tissue oxygenation. A biological relevance to cervical ripening/modeling of use of sPA imaging may be that, during cervical remodeling, that tissue hydration increases, and the collagen network disorganizes; that during ripening, tissue vascularization increases and intraamniotic infection increases a risk of preterm delivery and that inflammation may increase tissue blood perfusion as a compensatory process; and a continuous increment in pressure to the cervix due to fetal growth could reduce blood supply and lead to tissue hypoxia.

In embodiments, one or more images and one or more biomarker parameters of the cervical tissue at least partially based on the US and PA and VE signals may be generated in real-time, and the one or more images and the risk parameter on the display of the ultrasound machine. The VE signals may generate the one or more biomarker parameters of the cervical tissue including at least elasticity and viscosity of the cervical tissue that is the medium for the VE signals. The one or more biomarker parameters of the cervical tissue may include at least one of: a collagen to water ratio of the cervical tissue, a water content parameter of the cervical tissue, an oxygen saturation parameter of the cervical tissue, or a hemoglobin content parameter of the cervical tissue. In response to the water content parameter of the cervical tissue being representative of an increase of water content over a period of time to above a predetermined threshold, the risk parameter may be indicative of a risk of preterm delivery based on the water content parameter. In response to the collagen to water ratio being representative of an increase of water to collagen over a period of time to above a predetermined threshold, the risk parameter may be indicative of a risk of preterm delivery based on the collagen to water ratio. In response to the oxygen saturation parameter being representative of a reduction of oxygen saturation of the cervical tissue over a period of time to below a predetermined threshold, the risk parameter may be indicative of a risk of preterm delivery based on the oxygen saturation parameter. In response to the hemoglobin content parameter being representative of a reduction of hemoglobin content of the cervical tissue over a period of time to below a predetermined threshold, the risk parameter may be indicative of a risk of preterm delivery based on the hemoglobin content parameter.

Additionally, for a modality of VE imaging as described herein, a biomarker analysis may identify (a) unbiased shear elastic modulus and (b) shear viscosity of the cervical tissue. A biological relevance to cervical ripening/modeling of use of VE imaging may be that, during cervical remodeling, that tissue stiffness decreases per elasticity changes, and that proteoglycans, such as decorin, may be abundant in the cervix as a source of viscosity in the cervical tissue.

A signal may be "generated" by direct or indirect calculation or measurement, with or without the aid of a sensor.

For the purposes of describing and defining the present invention, it is noted that reference herein to a variable being a "function" of (or "based on") a parameter or another variable is not intended to denote that the variable is exclusively a function of or based on the listed parameter or variable. Rather, reference herein to a variable that is a "function" of or "based on" a listed parameter is intended to be open ended such that the variable may be a function of a single parameter or a plurality of parameters.

It is also noted that recitations herein of "at least one" component, element, etc., should not be used to create an inference that the alternative use of the articles "a" or "an" should be limited to a single component, element, etc.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A system for risk of preterm labor assessment during delivery comprising:
  one or more processors;
  one or more memory modules communicatively coupled to the one or more processors;

an ultrasound machine comprising a display and communicatively coupled to the one or more memory modules;
a probe device communicatively coupled to the ultrasound machine; and
machine readable instructions stored in the one or more memory modules that cause the system to perform at least the following when executed by the one or more processors:
  transmit a plurality of (ultrasound) US and (photoacoustic) PA and viscoelastic (VE) signals from the probe device toward cervical tissue of a cervix upon insertion of the probe device into a vaginal birth canal of a maternal pelvis including a fetus, wherein the transmitted PA signals comprise laser pulses configured to be tunable based on a change in wavelength, wherein the cervical tissue is a medium for the VE signals;
  receive, into the probe device, a plurality of reflected US and PA and VE signals via the probe device;
  transmit, via the probe device, the received plurality of reflected US and PA and VE signals to the ultrasound machine;
  generate one or more images and one or more biomarker parameters of the cervical tissue at least partially based on the US and PA and VE signals in real-time, wherein the one or more biomarker parameters of the cervical tissue comprise a collagen to water ratio of the cervical tissue;
  generate a risk parameter of preterm delivery of the fetus based on the one or more biomarker parameters of the cervical tissue, wherein in response to the collagen to water ratio being representative of an increase of water to collagen over a period of time to above a predetermined threshold, the risk parameter is indicative of a risk of preterm delivery based on the collagen to water ratio; and
  display the one or more images and the risk parameter on the display of the ultrasound machine.

2. The system of claim 1, wherein:
the probe device comprises an optical fiber assembly communicatively coupled to a laser and an active surface communicatively coupled to a transducer.

3. The system of claim 2, wherein:
the plurality of US signals are transmitted from the active surface of the probe device as a series of sound wave signals.

4. The system of claim 3, wherein:
the plurality of PA signals are transmitted from the optical fiber assembly as a series of laser pulse signals from the laser.

5. The system of claim 1, wherein the one or more biomarker parameters of the cervical tissue further comprise at least one of: a water content parameter of the cervical tissue, an oxygen saturation parameter of the cervical tissue, or a hemoglobin content parameter of the cervical tissue.

6. The system of claim 5, wherein in response to the water content parameter of the cervical tissue being representative of an increase of water content over a period of time for the water content parameter to above a predetermined threshold for the water content parameter, the risk parameter is indicative of a risk of preterm delivery based on the water content parameter.

7. The system of claim 5, wherein in response to the oxygen saturation parameter being representative of a reduction of oxygen saturation of the cervical tissue over a period of time for the oxygen saturation parameter to below a predetermined threshold for the oxygen saturation parameter, the risk parameter is indicative of a risk of preterm delivery based on the oxygen saturation parameter.

8. The system of claim 5, wherein in response to the hemoglobin content parameter being representative of a reduction of hemoglobin content of the cervical tissue over a period of time for the hemoglobin content parameter to below a predetermined threshold for the hemoglobin content parameter, the risk parameter is indicative of a risk of preterm delivery based on the hemoglobin content parameter.

9. The system of claim 1, wherein the plurality of US and PA signals are transmitted from the probe device toward the cervical tissue to generate a view of each of a sagittal plane and a transverse plane orthogonal to the sagittal plane and to generate a collagen degradation parameter as one of the one or more biomarker parameters based on a comparison of the sagittal plane and the transverse plane.

10. The system of claim 9, wherein the comparison of the sagittal plane and the transverse plane is indicative that collagen degradation measured over a period of time comprises a risk collagen degradation metric above a predetermined threshold representative of a cervical ripening to turn an anisotropic muscular cervix into a less muscular isotropic cervix, and the risk parameter is indicative of a risk of preterm delivery based on the risk collagen degradation metric.

11. The system of claim 1, wherein the VE signals generate the one or more biomarker parameters of the cervical tissue comprising at least elasticity and viscosity of the cervical tissue that is the medium for the VE signals.

* * * * *